(12) United States Patent
Paratore

(10) Patent No.: US 10,130,506 B2
(45) Date of Patent: Nov. 20, 2018

(54) CLOSURE SYSTEM FOR AN OSTOMY POUCH AND RELATED METHODS

(71) Applicant: Ostosolutions, LLC, Dover, DE (US)

(72) Inventor: Dominic A. Paratore, Manchester, MA (US)

(73) Assignee: OSTOSOLUTIONS, LLC, Dover, DE (US)

( * ) Notice: Subject to any disclaimer, the term of this patent is extended or adjusted under 35 U.S.C. 154(b) by 664 days.

(21) Appl. No.: 14/261,875

(22) Filed: Apr. 25, 2014

(65) Prior Publication Data

US 2014/0309604 A1    Oct. 16, 2014

Related U.S. Application Data

(63) Continuation-in-part of application No. 13/844,443, filed on Mar. 15, 2013, which is a continuation-in-part of application No. 12/660,640, filed on Mar. 2, 2010, now Pat. No. 8,690,848.

(51) Int. Cl.
*A61F 5/44* (2006.01)
*A61F 5/445* (2006.01)

(52) U.S. Cl.
CPC .......... *A61F 5/4407* (2013.01); *A61F 5/4404* (2013.01); *A61F 5/445* (2013.01)

(58) Field of Classification Search
CPC combination set(s) only.
See application file for complete search history.

(56) References Cited

U.S. PATENT DOCUMENTS

| 2,595,934 | A | | 5/1952 | Ginsburg |
| 2,639,710 | A | | 5/1953 | Fazio |
| 2,721,553 | A | | 10/1955 | Perry |
| 3,089,493 | A | * | 5/1963 | Galindo ................. A61F 5/445 |
| | | | | 604/342 |
| 3,523,534 | A | | 8/1970 | Nolan |

(Continued)

FOREIGN PATENT DOCUMENTS

| DK | 177034 B1 * | 2/2011 | ............. A61F 5/445 |
| GB | 2 193 098 A | 8/1986 | |

(Continued)

OTHER PUBLICATIONS

Supplementary European Search Report, Application No. EP 11751015.6, date of completion of the search Jul. 6, 2017 (6pgs.).

(Continued)

*Primary Examiner* — Tatyana Zalukaeva
*Assistant Examiner* — Guy K Townsend
(74) *Attorney, Agent, or Firm* — Mintz Levin Cohn Ferris Glovsky and Popeo, P.C.

(57) ABSTRACT

An ostomy closure is disclosed for sealing an ostomy pouch after use and removal from an ostomy mounting plate. The ostomy closure may comprise a flexible storage bag having a bag base and a bag opening and define a bag chamber. The bag base may couple to an exterior surface of the ostomy pouch. The bag opening may retract over the ostomy pouch and define a bag pouch enclosure for encapsulating the ostomy pouch within the bag chamber to prevent leakage of contents within the ostomy pouch from and through flexible storage bag upon being securely sealed at an opened end.

15 Claims, 40 Drawing Sheets

(56) References Cited

U.S. PATENT DOCUMENTS

| | | | |
|---|---|---|---|
| 3,901,401 A | 8/1975 | Lynn et al. | |
| 4,468,227 A * | 8/1984 | Jensen | A61M 27/00 600/573 |
| 4,533,967 A | 8/1985 | Conly et al. | |
| 4,701,169 A | 10/1987 | Steer | |
| 4,872,869 A | 10/1989 | Johns | |
| 5,520,670 A | 5/1996 | Blum | |
| 5,690,621 A | 11/1997 | Canela | |
| 6,106,508 A | 8/2000 | Lavender | |
| 6,537,261 B1 | 3/2003 | Steer et al. | |
| 6,709,422 B2 * | 3/2004 | Hessel | A61F 5/448 604/342 |
| 6,902,551 B2 | 6/2005 | Hansen et al. | |
| 6,964,654 B2 * | 11/2005 | Fanti | A61F 5/445 604/333 |
| 7,468,056 B2 | 12/2008 | Burt | |
| 7,569,038 B1 | 8/2009 | Salem, Jr. | |
| 7,722,585 B2 | 5/2010 | Falconer et al. | |
| 7,722,586 B2 | 5/2010 | Mullejans et al. | |
| 7,745,681 B1 | 6/2010 | Ferguson | |
| 7,819,850 B2 | 10/2010 | Mullejans et al. | |
| 7,947,025 B2 | 5/2011 | Bugilino et al. | |
| 8,070,737 B2 | 12/2011 | Cline et al. | |
| 8,092,437 B2 | 1/2012 | Cline | |
| 8,096,980 B2 | 1/2012 | Cline | |
| 8,100,875 B2 | 1/2012 | Cline et al. | |
| 8,105,298 B2 | 1/2012 | Mullejans et al. | |
| 8,142,406 B2 | 3/2012 | Blum | |
| 8,343,121 B2 | 1/2013 | Cramer et al. | |
| 8,690,848 B2 * | 4/2014 | Cason | A61F 5/445 220/495.1 |
| 2002/0077611 A1 | 6/2002 | Von Dyck et al. | |
| 2002/0082570 A1 * | 6/2002 | Mishima | A61F 5/451 604/332 |
| 2002/0114539 A1 | 8/2002 | Strevey et al. | |
| 2002/0133134 A1 | 9/2002 | Wilbon | |
| 2003/0023210 A1 | 1/2003 | Bedard et al. | |
| 2003/0073962 A1 * | 4/2003 | Olsen | A61F 5/4407 604/327 |
| 2004/0059306 A1 | 3/2004 | Tsai et al. | |
| 2004/0087920 A1 | 5/2004 | Etheredge, III | |
| 2004/0111072 A1 | 6/2004 | McKissick | |
| 2004/0191459 A1 | 9/2004 | Driesten | |
| 2005/0177119 A1 | 8/2005 | Tsai et al. | |
| 2005/0182379 A1 | 8/2005 | Olsen et al. | |
| 2005/0247432 A1 | 11/2005 | Bhatti et al. | |
| 2006/0200101 A1 | 9/2006 | Mullejans et al. | |
| 2007/0080092 A1 | 4/2007 | DeLuca | |
| 2008/0004580 A1 | 1/2008 | Mullejans et al. | |
| 2008/0039809 A1 | 2/2008 | Kamen et al. | |
| 2008/0243098 A1 | 10/2008 | Hewitt | |
| 2009/0163883 A1 | 6/2009 | Christensen et al. | |
| 2009/0247969 A1 | 10/2009 | Nishtala et al. | |
| 2009/0299309 A1 | 12/2009 | Fenton | |
| 2010/0022976 A1 | 1/2010 | Weig | |
| 2010/0069859 A1 | 3/2010 | Weig | |
| 2010/0100064 A1 | 4/2010 | Sambasivam | |
| 2010/0174253 A1 | 7/2010 | Cline | |
| 2010/0211033 A1 | 8/2010 | Blum | |
| 2011/0028924 A1 * | 2/2011 | Murray | A61F 5/4407 604/332 |
| 2011/0040269 A1 | 2/2011 | Cline | |
| 2011/0071485 A1 | 3/2011 | Foley et al. | |
| 2011/0092929 A1 | 4/2011 | Weig | |
| 2011/0118684 A1 | 5/2011 | Nguyen-DeMary | |
| 2011/0178483 A1 | 7/2011 | Oberholtzer et al. | |
| 2011/0213321 A1 * | 9/2011 | Fattman | A61F 5/443 604/344 |
| 2011/0213322 A1 | 9/2011 | Cramer | |
| 2011/0313378 A1 | 12/2011 | Gregory | |
| 2012/0109086 A1 | 5/2012 | Tsai | |
| 2012/0179124 A1 | 7/2012 | Nguyen-Demary | |
| 2013/0144236 A1 * | 6/2013 | Brandt | A61F 5/445 604/344 |
| 2014/0309604 A1 * | 10/2014 | Paratore | A61F 5/4407 604/332 |

FOREIGN PATENT DOCUMENTS

| | | |
|---|---|---|
| WO | WO 98/38952 | 9/1998 |
| WO | WO-2011/109079 A1 | 9/2011 |
| WO | WO-2011/124225 A1 | 10/2011 |
| WO | WO-2015/164804 A1 | 10/2015 |

OTHER PUBLICATIONS

Extended European Search Report dated Dec. 11, 2017, for EP Application No. 15783138.9, filed Apr. 24, 2015, 7 pages.

* cited by examiner

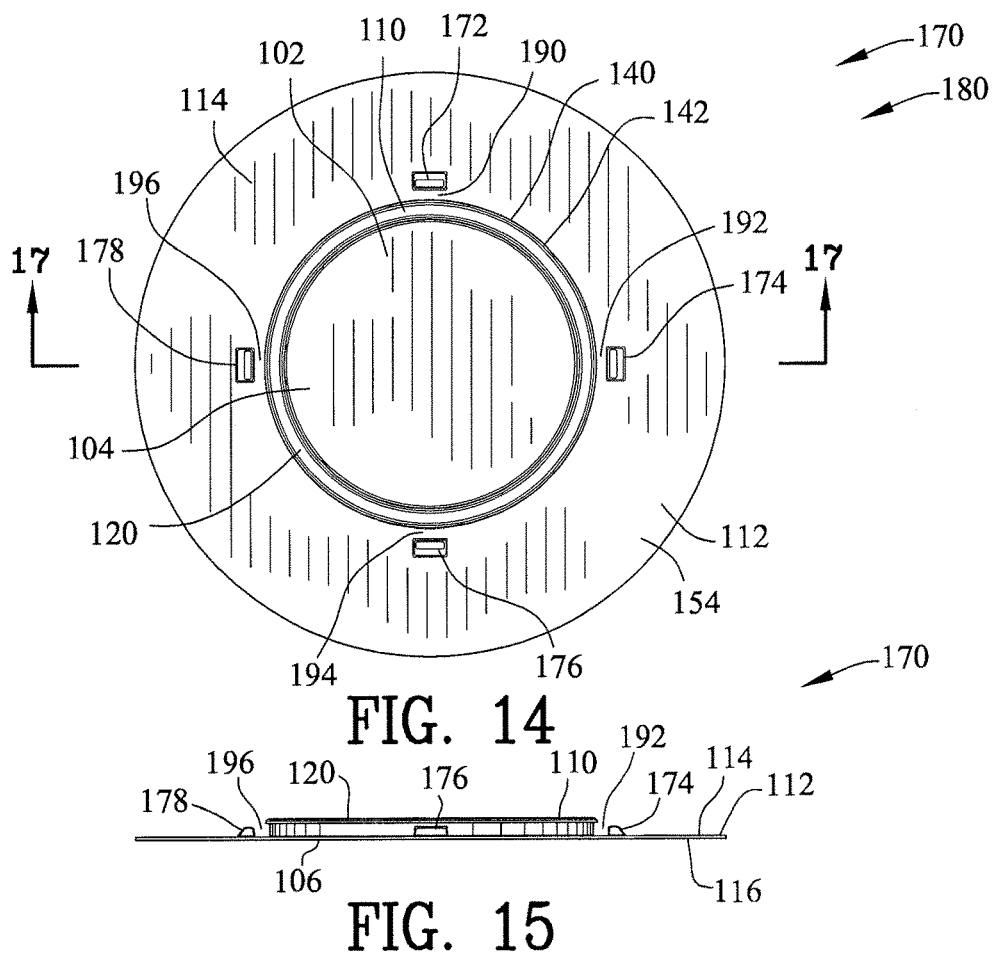
FIG. 14
FIG. 15
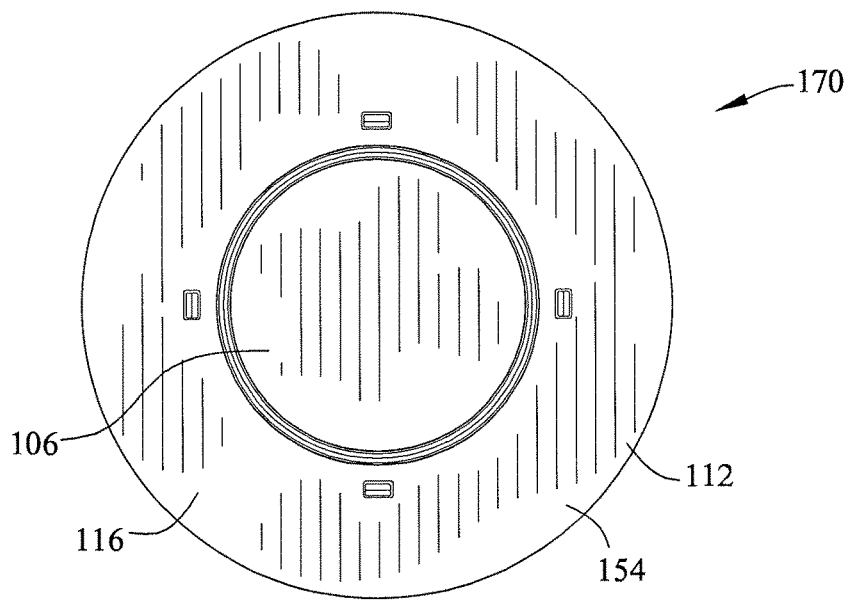
FIG. 16

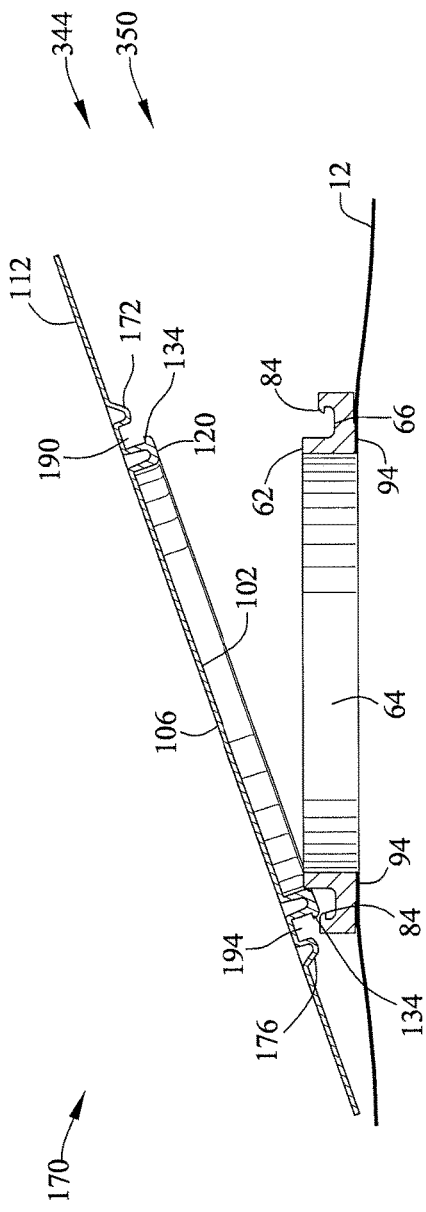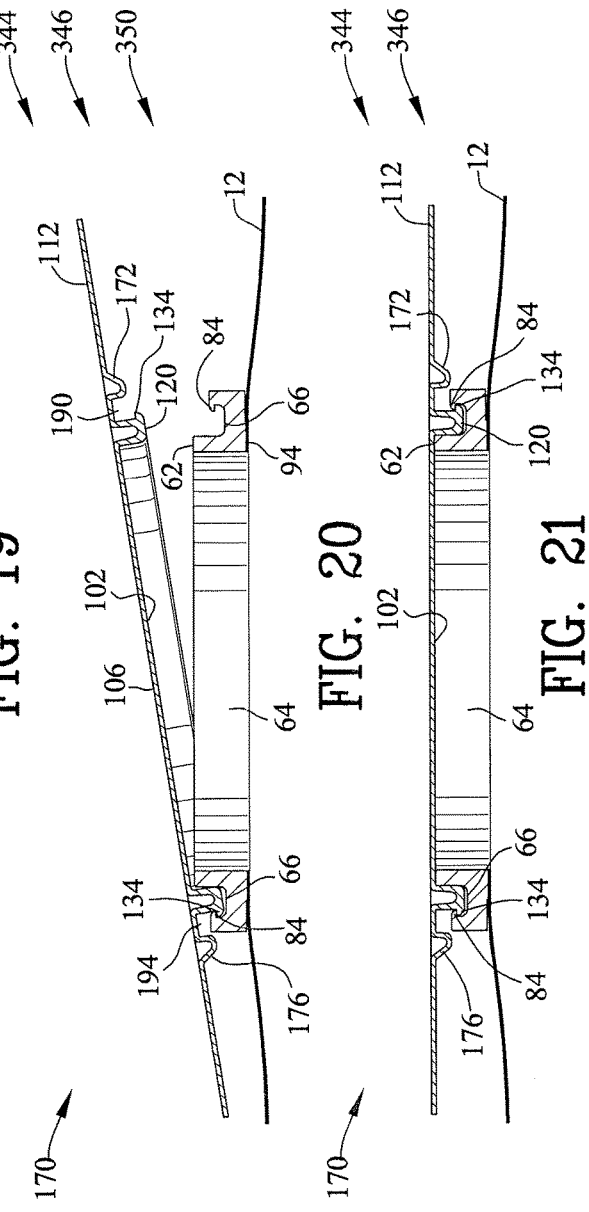

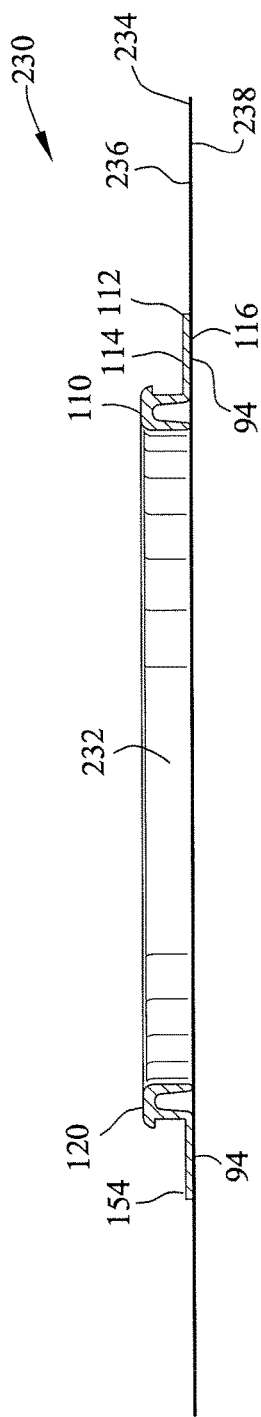
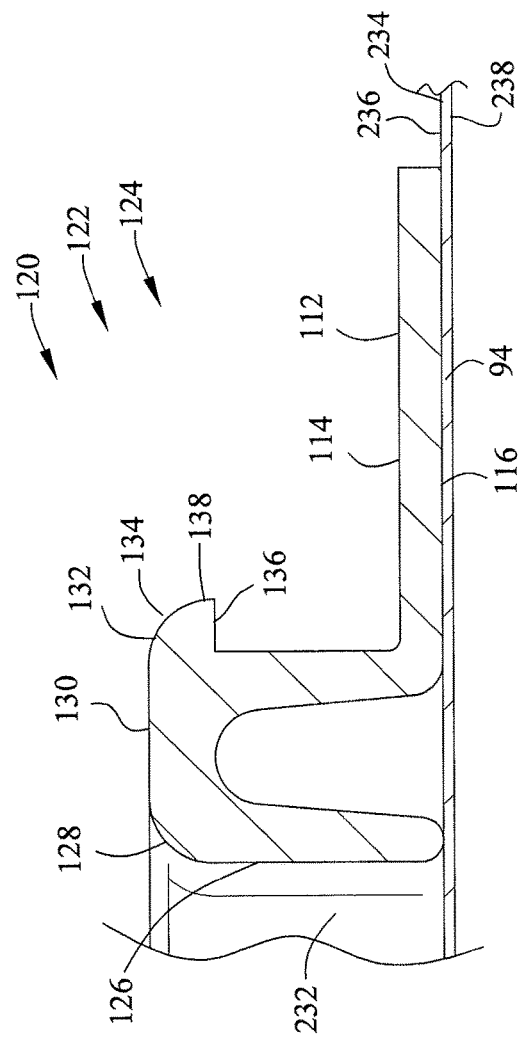
FIG. 31
FIG. 32

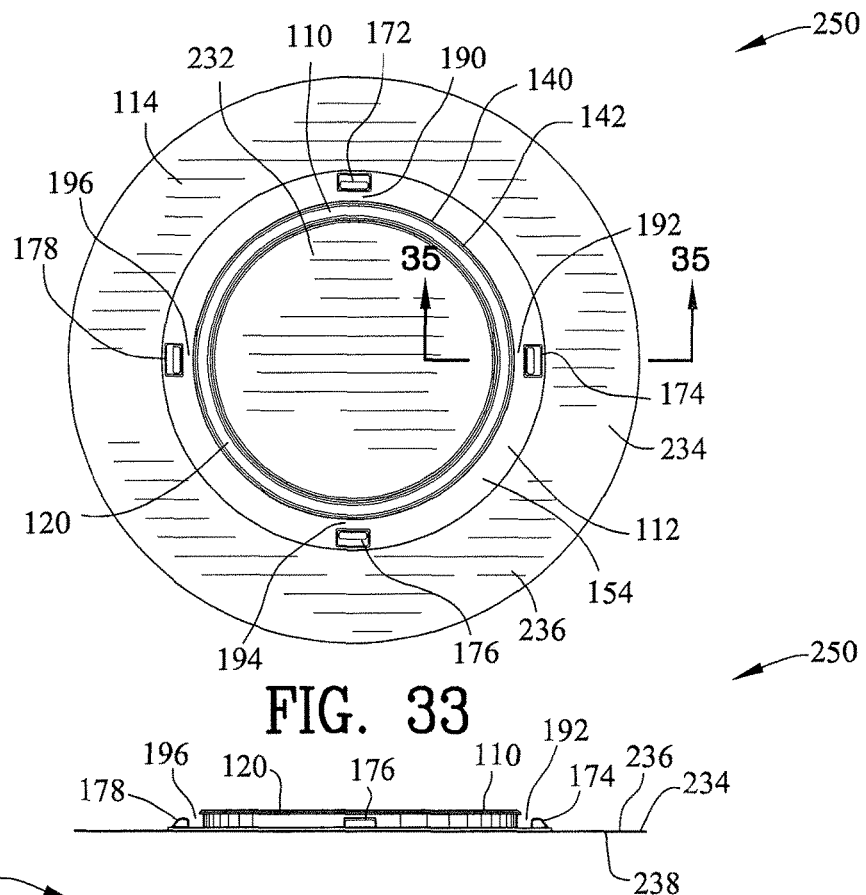
FIG. 33
FIG. 34
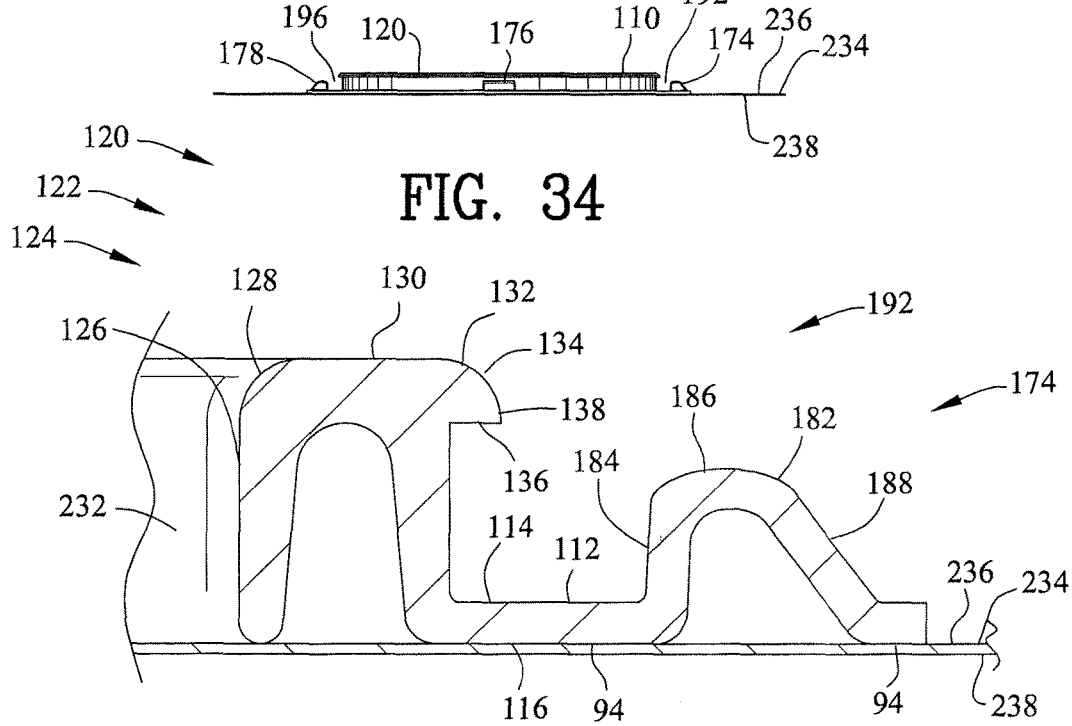
FIG. 35

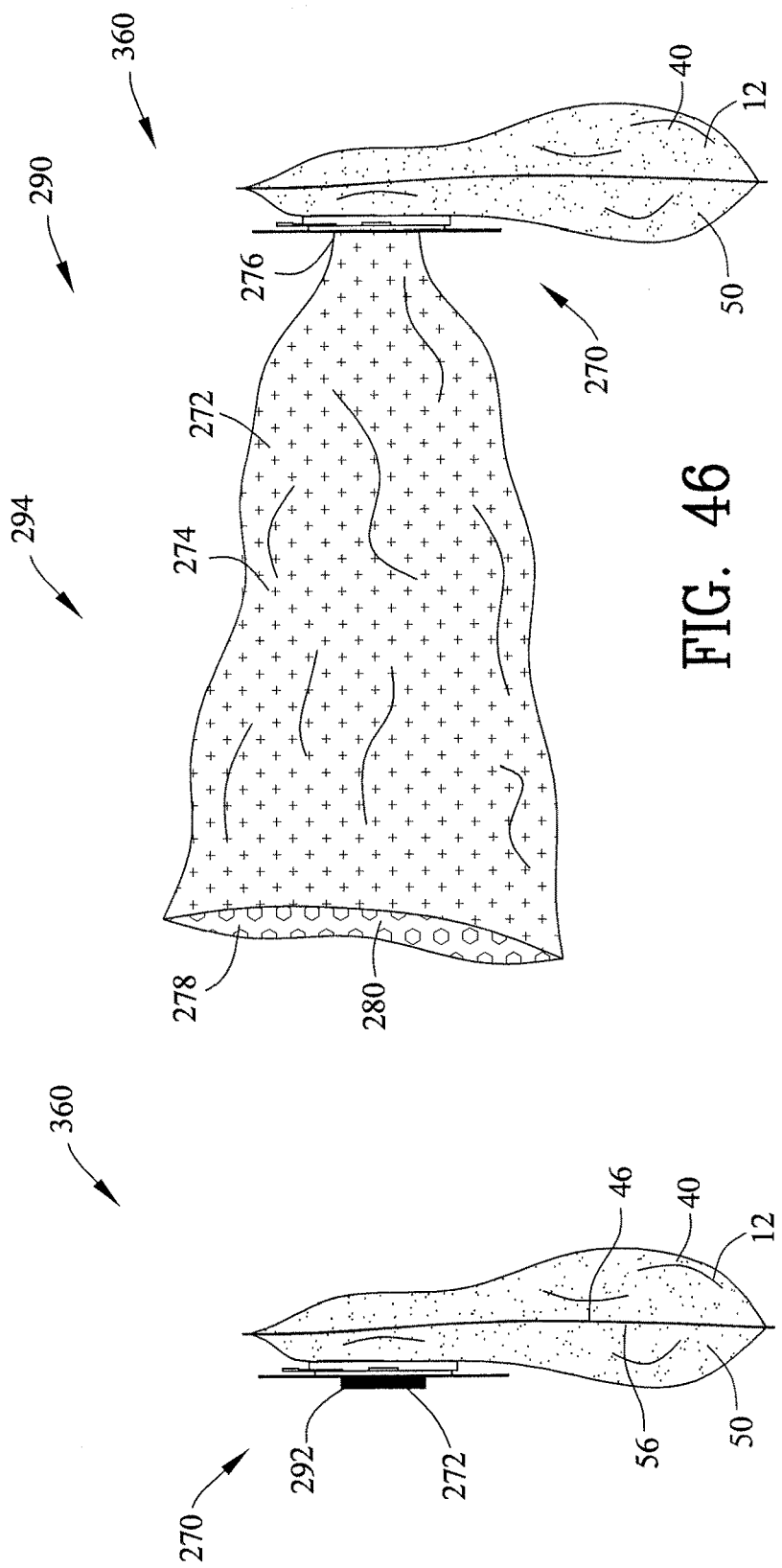

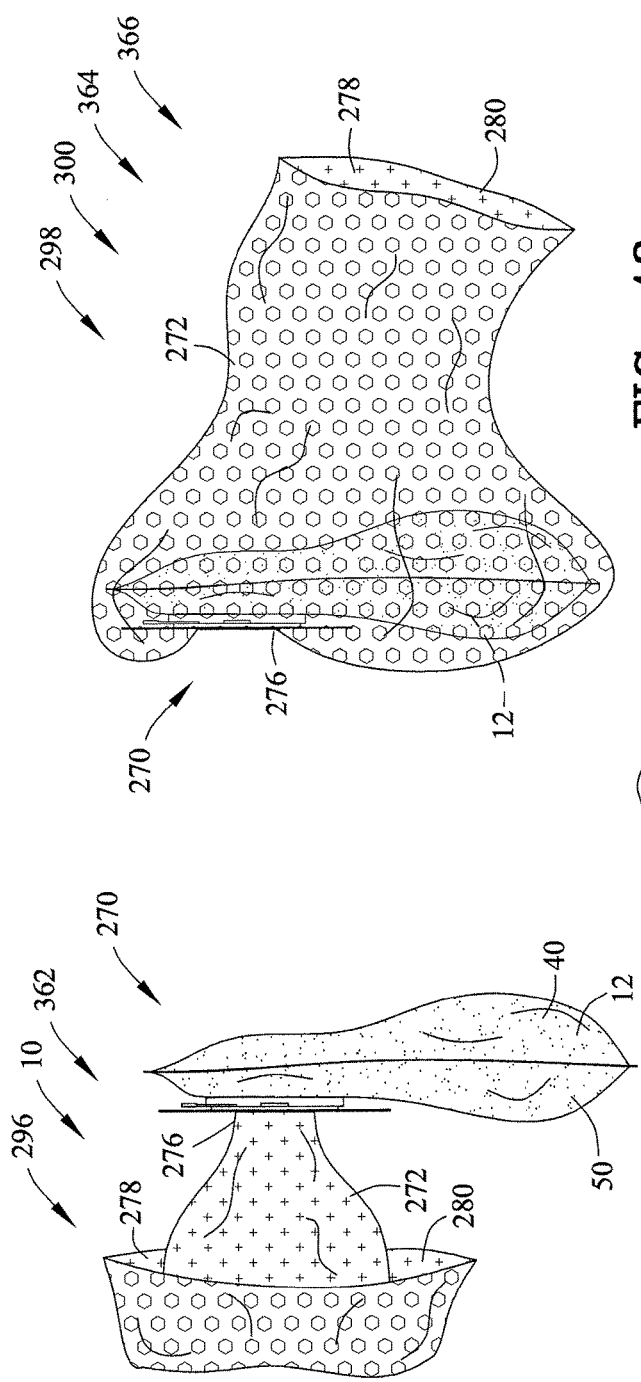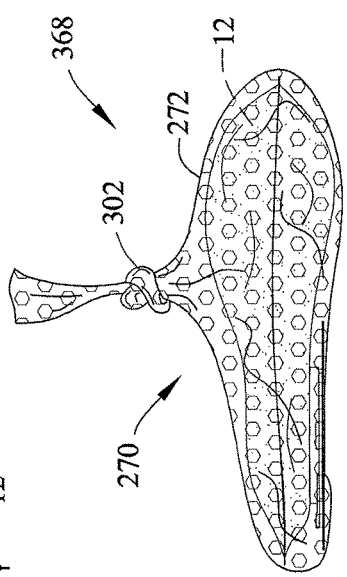

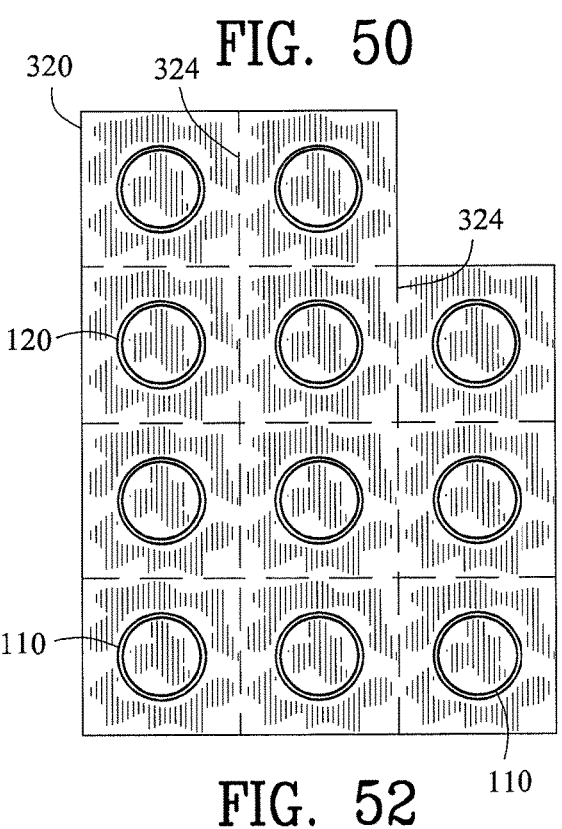
FIG. 50
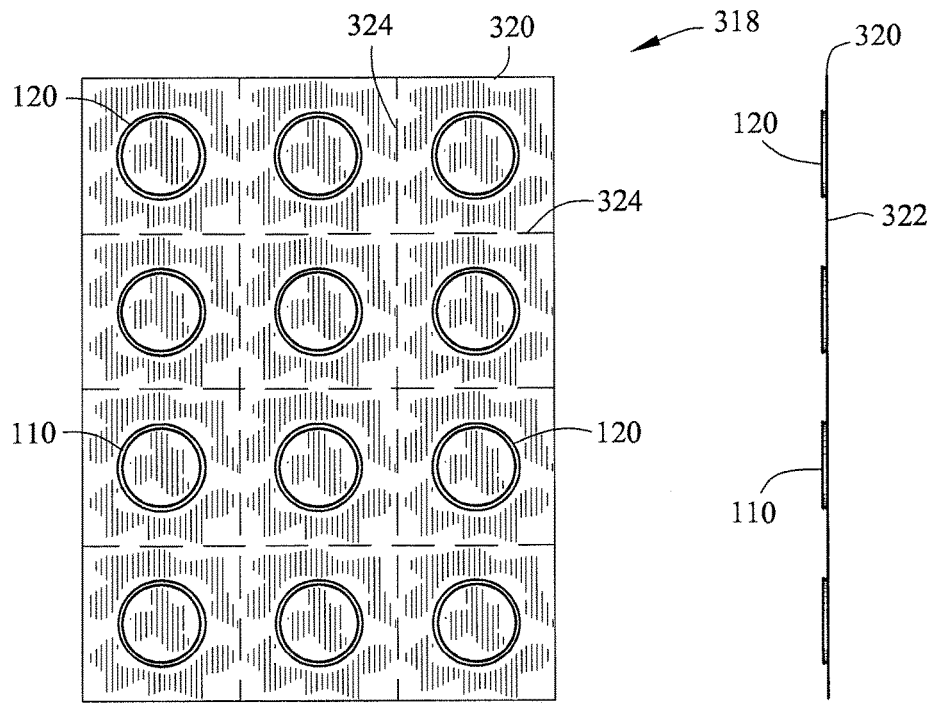
FIG. 51
FIG. 52
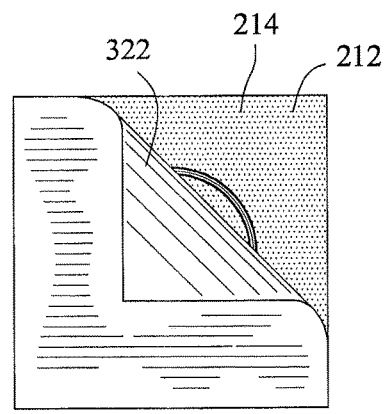
FIG. 53

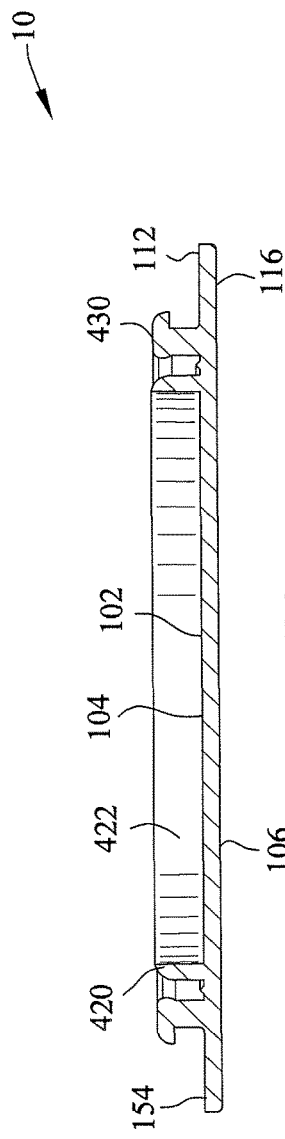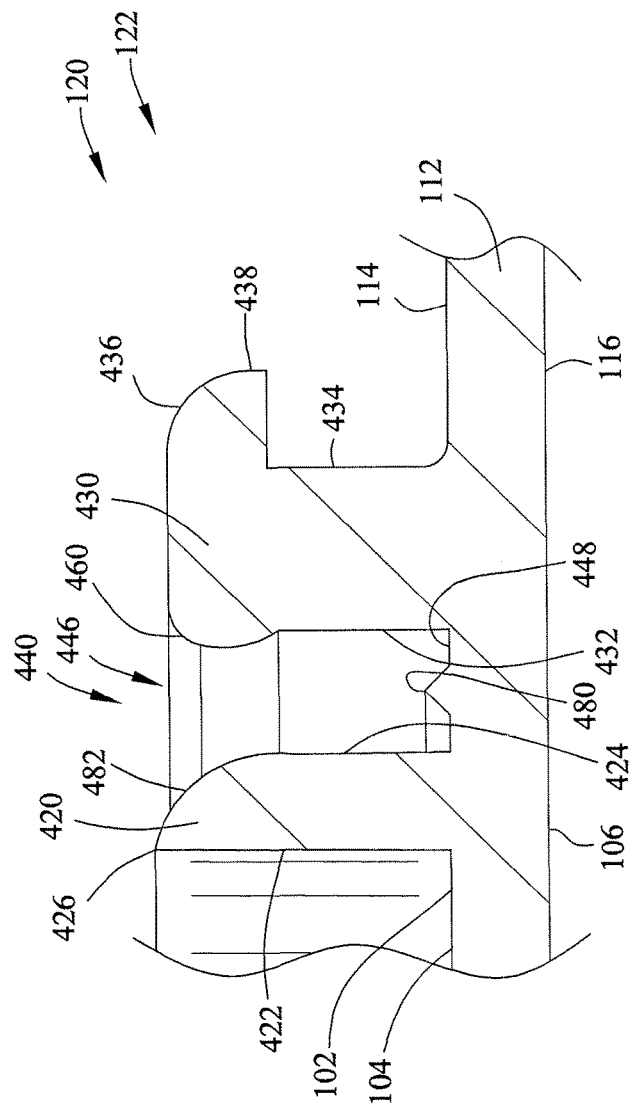

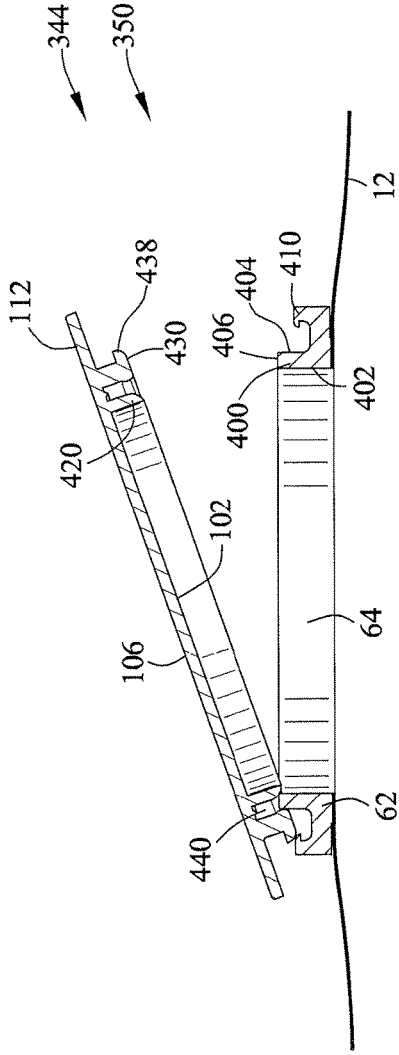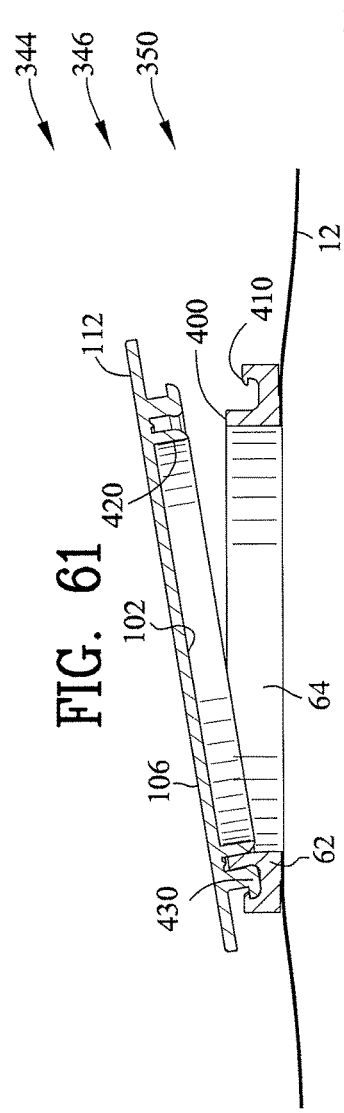

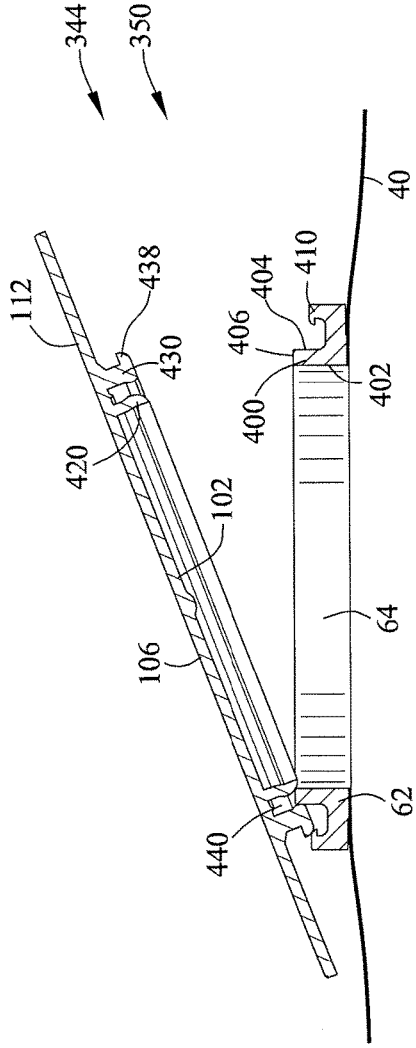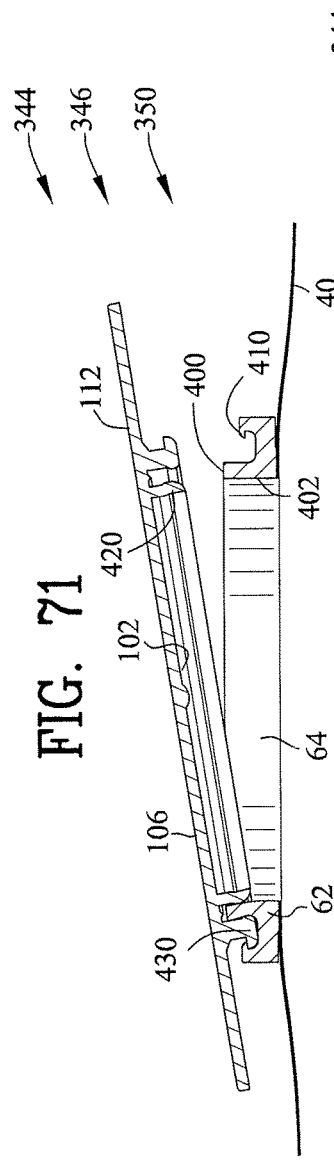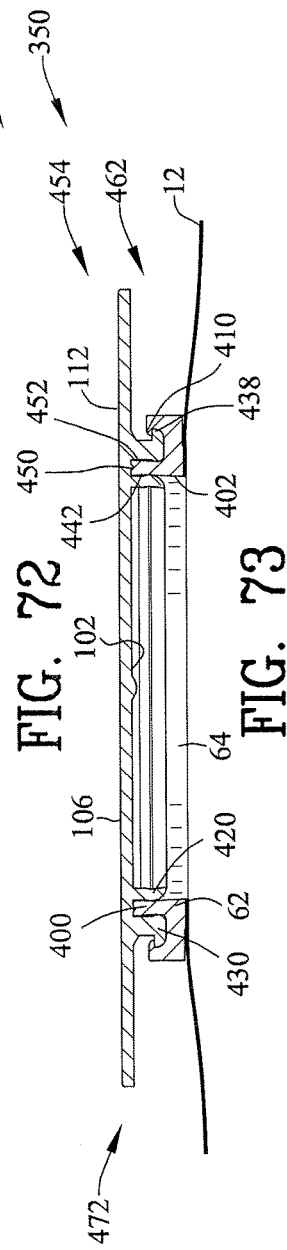

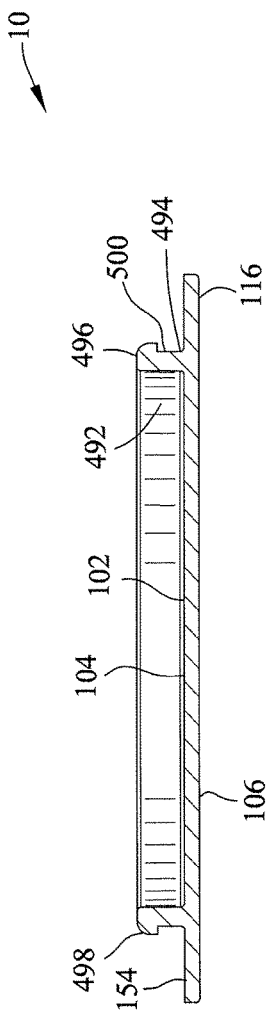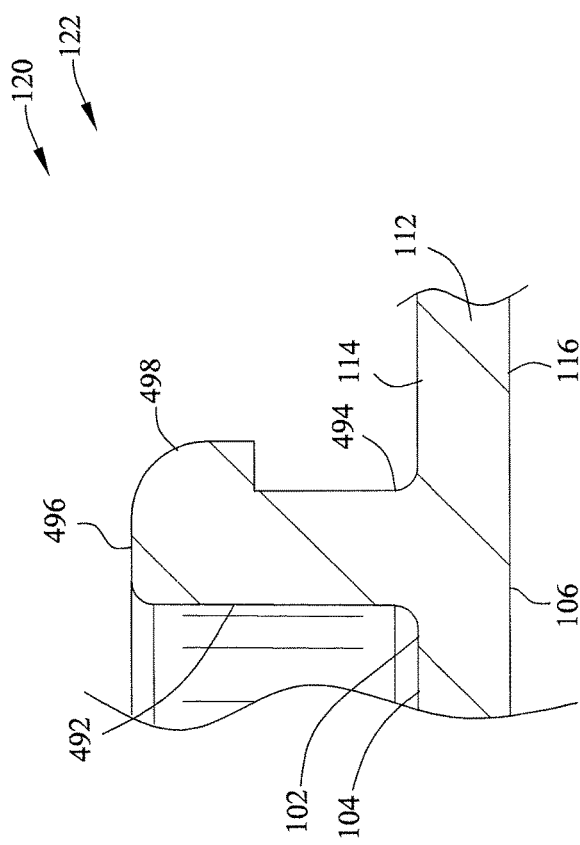
FIG. 79
FIG. 80

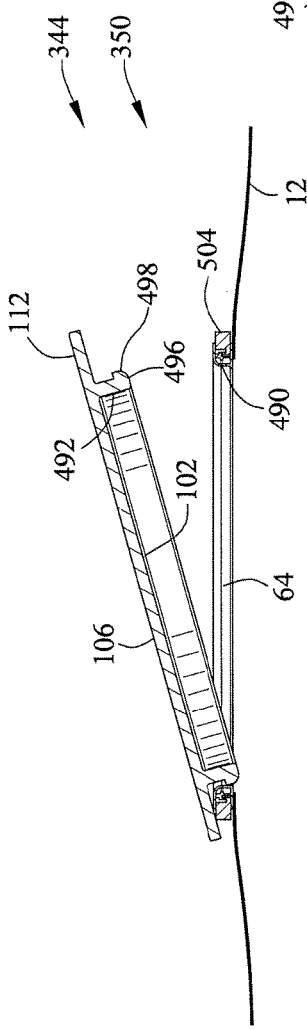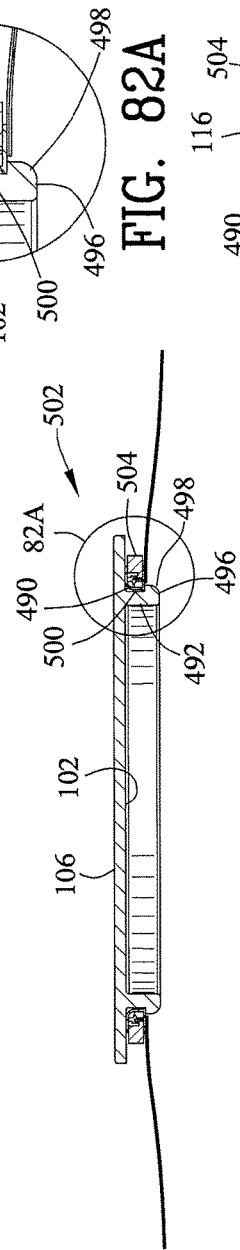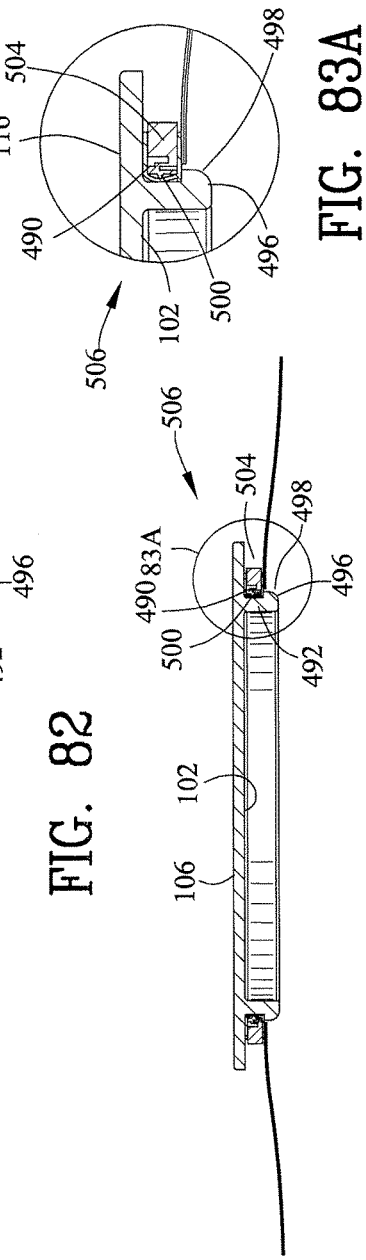

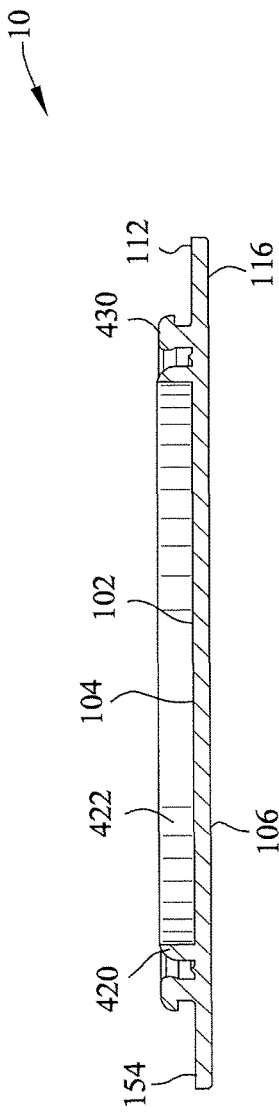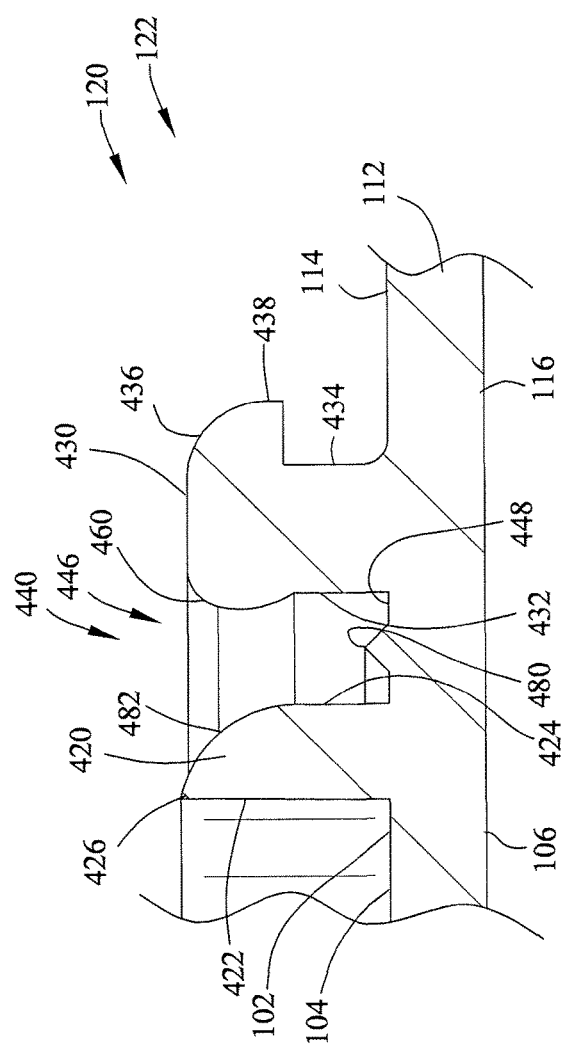

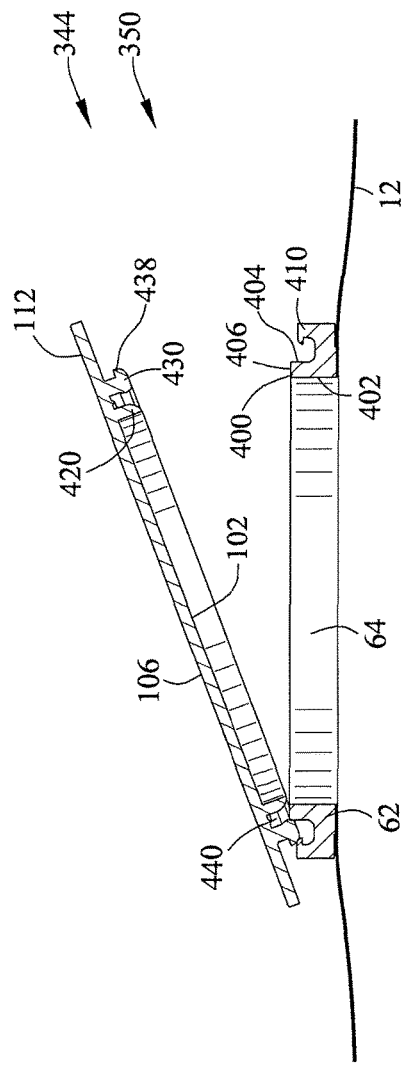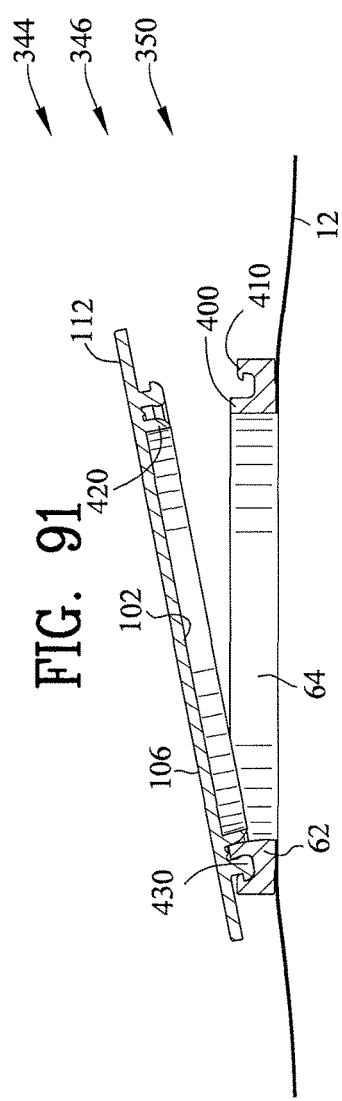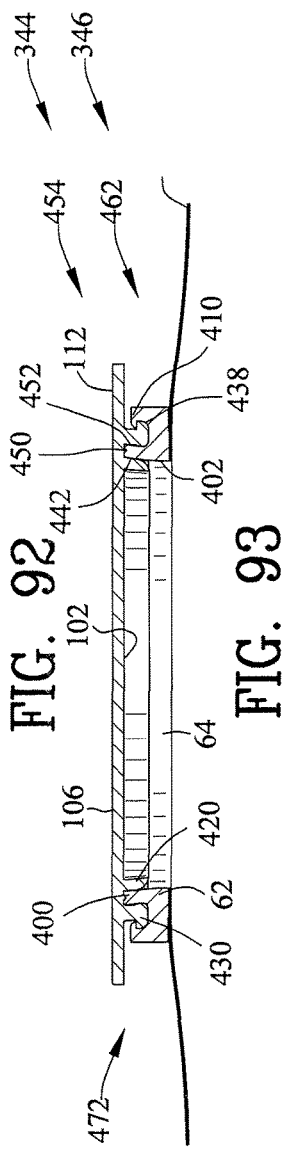

CLOSURE SYSTEM FOR AN OSTOMY POUCH AND RELATED METHODS

CROSS-REFERENCE TO RELATED APPLICATIONS

This application is a continuation-in-part of U.S. patent application Ser. No. 13/844,443 filed on Mar. 15, 2013, which claims priority to U.S. patent application Ser. No. 12/660,640 filed on Mar. 2, 2010, now U.S. Pat. No. 8,690,848, the disclosures of which are incorporated herein by reference in their entireties.

FIELD

This subject matter of the disclosure relates to closures and more particularly to an improved ostomy pouch closure.

BACKGROUND

Due to various intestinal or rectal diseases such as cancer or inflammatory bowel disease, many people require a surgical procedure whereby the diseased portion of the intestine is removed and the healthy portion of the intestine is attached to the abdominal wall. Surgical diversion procedures involving the small intestine are referred to as illeostomies and those involving the large intestine or rectum are referred to as colostomies. The end of the intestine or rectum is sutured to the skin forming a stoma. Waste products discharged from the stoma are collected using an ostomy appliance. An ostomy appliance conventionally includes a wafer and an ostomy pouch.

Ostomy pouches are secured to the skin of the wearer using a sealing material, or wafer, that adheres to the skin and surrounds the stoma. The appliance may be designed as a one-piece device with a wafer attaching directly to the wearer and then connecting to a pouch with a drain at the lower end of the pouch. This device is reusable until the wearer needs to replace the entire appliance.

Alternatively the appliance may be manufactured in two pieces. The first piece is a separate wafer with a central opening sized to fit around the stoma. This wafer has a flange in varying sizes to accommodate a wide range of stoma sizes and has adhesive properties that allow it to be affixed to the wearer over the stoma. The second piece is an ostomy pouch having a corresponding flange that snaps into the wafer flange. The ostomy pouch has a flexible wall with an opening to receive waste products from the stoma.

The two-piece appliance may have an ostomy pouch that is either a closed-end pouch, such that the pouch must be replaced after each use or an opened-end pouch that is drainable, such that the pouch can be reused until the wearer needs to replace it, usually after a day or two. Advantageously the drainable pouches may have a tapered open end to allow the user to discharge the stool into a conventional toilet and then seal the pouch using a specially-designed clip or other closure. Conversely the drainable pouches are cumbersome to empty, carry an on-going risk of clip or closure failure and are difficult to empty in a hygienic manner.

The advantage of the closed-end pouches is that they are designed for one-time usage, making them ideal for everyday use, special occasions or intimate moments. Closed-end pouches eliminate the need to manipulate a clip or closure to empty the pouch and there is no need for messy draining of stool or an uncomfortable clip to worry about. These pouches can be emptied much faster and a toilet area is preferable but not required. The user simply removes the pouch and discards it in a trash receptacle. The disadvantage of this system is that the used pouches cannot be flushed down a toilet and must be discarded in the trash. As a result, the user is faced with the embarrassing challenge of disposing of a highly-odorous pouch numerous times per day. This is a difficult challenge in the privacy of one's home and especially so in the workplace, restaurants, and other social settings. Several devices of the prior art have had varying degrees of success in solving these problems.

U.S. Pat. No. 3,901,401 to Lynn et al. discloses a safety closure for containers wherein the neck of the container has a continuous encircling rib and the closure has an internal bead formation that snaps over the rib. The rib on the container has a portion of reduced radius to facilitate snapping the closure off the container. The container has a flange that lies below the closure and has a notched portion defining the release position of the closure. The closure has a tab that is not accessible due to the presence of the flange on the container excepting when the tab is in alignment with the notch. There are protuberances on either the continuous rib of the container or the interior of the closure that take up the slack in a radial direction normally present due to manufacturing tolerance.

U.S. Pat. No. 4,468,227 to Jensen discloses a wound drainage device in the form of a flexible pouch having top and bottom walls and having pleated side walls that allow the top wall to be lifted a limited distance without transmitting appreciable lifting or tensioning forces to the bottom wall when the bottom wall is surgically apertured and secured about a wound site. The top wall includes an access opening having a flanged locking ring of flexible plastic extending thereabout. A removable closure cap is attached to the access opening, the cap having a flat rim of flexible plastic with circumferential locking ribs releasably and sealingly engaging a series of mating ribs provided by the flanged portion of the ring.

U.S. Pat. No. 4,872,869 to Johns discloses a low profile ostomy device that includes an ostomy pouch with an opening, a first coupling member attached to the ostomy pouch at the opening, and a second coupling member for attachment to a user's body. The first and second coupling members are engaged by joining an engaging element on each of the members, the engagement providing a tight mechanical seal between the members within the ostomy pouch.

U.S. Pat. No. 5,690,621 to Canela discloses a drainable pouch for colostomy patients with a stoma and includes a valve for selectively releasing the gases trapped within the pouch. The valve assembly is removably mounted permitting a user to rinse the interior of the pouch from the uppermost portion. The valve also contains an odor suppressant filter that may include an impregnated fragrance. A cap member is used to cover the outlet spout. A sheet having cooperative dimensions and made out of a non-transparent material is used to conceal the pouch from public view.

U.S. Pat. No. 6,106,508 to Lavender discloses an ostomy pouch having a first and second panels of flexible material sealed to each other around the edges to form a pouch and a aperture for receiving waste product from a stoma. A seal is provided on the inner surfaces of the two panels to seal waste products in the pouch before the pouch is removed from the side of a wearer.

U.S. Pat. No. 6,964,654 to Fanti discloses a disposable cover for enclosing the outlet spout of a drainable stoma pouch. The cover includes front and rear walls sealed along side and bottom edges, with an unsealed upper edge. Preferably, one or more stiffening ribs extend longitudinally across the front and rear walls near the unsealed upper edge. The presence, spacing and relative orientation of such ribs on the external surfaces of the front and rear walls render the disposable cover self-opening such that it may be easily placed over to enclose the outlet spout of a drainable stoma pouch. Once positioned, the cover is clamped onto the tail section of the pouch to provide effective odor and moisture containment therein.

U.S. Pat. No. 7,468,056 to Burt discloses a colostomy pouch with a vent and a method for venting gas collected in the colostomy pouch. A dual vent and cap assembly attached to a colostomy pouch vents gas trapped in the pouch either continuously or as periodically desired by a user. A method for venting gas collected in the colostomy pouch provides that replacement and/or cleaning of the colostomy pouch is reduced. A method of using a disposable sleeve in combination with a clip may be used to hygienically clean the colostomy pouch.

United States Patent Application Publication No. 2004/0111072 to McKissick disclosing a display arrangement for organizing and presenting supplies and implements needed for ostomy care has at least one display surface for the supplies and implements, the display surface having alpha-numerically-sequenced indicia disposed thereon. The indicia include at least one indicator for at least one skin preparation product, at least one indicator for stoma measurement, at least one indicator for at least one wafer cutting implement, at least one indicator for a wafer, at least one indicator for at least one adhesive product and at least one indicator for at least a pouch.

None of these systems, arrangements and/or methods however completely satisfies the need for a complete solution to the aforementioned issues.

It is therefore an objective of the disclosure to provide an improved system, apparatus and/or methodology for sealing and disposing an ostomy appliance and/or an ostomy pouch in a clean, discrete, hygienic and odor-free manner.

Another objective of the disclosure may be to provide an improved apparatus for sealing an ostomy appliance or an ostomy pouch following its removal from the stoma of a patient in an odor-free manner.

It is also an objective of the disclosure may be to provide an improved apparatus for maintaining the contents of an ostomy appliance and/or ostomy pouch and any odor released from the contents within the ostomy pouch to facilitate the odor-proof disposal of the ostomy pouch.

Another objective of the disclosure may be to provide an improved apparatus for the hygienic disposal of an ostomy appliance and/or ostomy pouch and its contents following the removal from the stoma of a colostomy patient.

Another objective of the disclosure may be to provide an improved apparatus that is simple for a colostomy patient to use.

Another objective of the disclosure may be to provide an improved apparatus that is easy to cost effectively produce.

The foregoing has outlined some of the more pertinent objects of the disclosure. These objects should be construed as being merely illustrative of some of the more prominent features and applications thereof. Other beneficial results can be obtained by modifying the subject matter of the disclosure within the scope of the subject matter of the disclosure. Other objectives in a full understanding of the disclosure may be had by referring to the following sections of this disclosure, including the appended claims, taken in conjunction with the accompanying drawings.

SUMMARY

Embodiments of the disclosure provided herein relate to an ostomy closure, such as for example a storage bag, for encapsulating or otherwise sealing an ostomy pouch after use and removal from an ostomy pouch mounting plate. The ostomy pouch mounting plate may be secured to an individual. The ostomy pouch may have a first flexible layer coupled to a second flexible layer for defining an ostomy chamber therein. An ostomy pouch member may convey stool from the individual into the ostomy chamber. The ostomy pouch in some embodiments may disengage from the ostomy pouch mounting plate to the individual for disposal of the stool. The ostomy closure may comprise a flexible storage bag having a bag base and a bag opening and define a bag chamber. The bag base may couple to an exterior surface of the ostomy pouch. The bag opening may in some embodiments retract over the ostomy pouch and define a bag pouch enclosure for encapsulating the ostomy pouch within the bag chamber to prevent leakage of contents within the ostomy pouch from and through flexible storage bag.

In some embodiments, subject matter of the disclosure may relate to an ostomy closure for sealing an ostomy pouch after use and removal from an ostomy mounting plate, wherein the ostomy closure includes a flexible storage bag having a first portion and a second portion. The first portion may include a first bag chamber extending between a first bag base and a first bag opening. The first bag chamber may encapsulate the ostomy pouch within the first bag chamber and couple to the ostomy pouch along any portion of the ostomy pouch. The second portion may include a second bag chamber extending between a second bag base and a second bag opening. The second portion may couple to the first portion in some embodiments. The second bag opening may retract over the second portion and the ostomy pouch for defining a bag pouch enclosure. A bag closure may engage the second bag chamber for encapsulating the first portion and the ostomy pouch within the second bag chamber.

The foregoing has outlined rather broadly the more pertinent and important features of the subject matter of the disclosure in order that the detailed description that follows may be better understood so that the present contribution to the art can be more fully appreciated. Additional features of the subject matter of the disclosure will be described hereinafter which form the subject of the claims of the subject matter of the disclosure. It should be appreciated by those skilled in the art that the conception and the specific embodiments disclosed may be readily utilized as a basis for modifying or designing other structures for carrying out the same purposes of the subject matter of the disclosure. It should also be realized by those skilled in the art that such equivalent constructions do not depart from the spirit and scope of the subject matter of the disclosure as set forth in the appended claims.

BRIEF DESCRIPTION OF THE DRAWINGS

For a fuller understanding of the nature and objects of the subject matter of the disclosure, reference should be made to the following detailed description taken in connection with the accompanying drawings in which:

FIG. 14 is a top view of a second embodiment for an ostomy closure including an aligning tab for defining an aligning channel between the aligning tab and a cap flange;

FIG. 15 is a side view of FIG. 14;

FIG. 16 is a bottom view of FIG. 14;

FIG. 19 is a view similar to FIG. 17 illustrating an aligning channel centering the ostomy closure relative to a pouch flange on the ostomy pouch;

FIG. 20 is a view similar to FIG. 19 illustrating a cap flange of the ostomy closure coupling with the pouch flange of the ostomy pouch;

FIG. 21 is a view similar to FIG. 20 illustrating a cap locking member of the ostomy closure engaging a pouch locking member of the pouch flange;

FIG. 31 is a sectional view along line 28-28 in FIG. 8;

FIG. 32 is an enlarged portion of FIG. 31;

FIG. 33 is a top view of a fifth embodiment for an ostomy closure ostomy closure including an flexible sheet coupled to the cap flange for covering the cap flange aperture and an aligning tab for defining an aligning channel between the aligning tab and a cap flange;

FIG. 34 is a side view of FIG. 33;

FIG. 35 is an enlarged sectional view along line 35-35 in FIG. 33;

FIG. 45 is a side elevational view of the ostomy closure of FIG. 42 engaged with the ostomy pouch;

FIG. 46 is a view similar to FIG. 45 illustrating the flexible storage bag expanding the flexible storage bag from the ostomy closure;

FIG. 47 is a view similar to FIG. 46 illustrating a bag opening of the flexible storage bag retracting over the flexible storage bag;

FIG. 48 is a view similar to FIG. 47 illustrating the bag opening of the flexible storage bag retracting over the ostomy closure and the ostomy pouch;

FIG. 49 is a view similar to FIG. 48 illustrating a had closure engaging the flexible storage bag for encapsulating both the ostomy closure and the ostomy pouch;

FIG. 50 is a top view of an eighth embodiment for a sheet of ostomy closures;

FIG. 51 is a side view of FIG. 50;

FIG. 52 is a view similar to FIG. 50 wherein a single ostomy closure has been removed along a perforated edge;

FIG. 53 is a rear view of the single ostomy closure removed from FIG. 52 wherein an adhesive backing sheet is being removed from a cap adhesive layer;

FIG. 59 is a sectional view of FIG. 56;

FIG. 60 is an enlarged portion of FIG. 59;

FIG. 61 is a view of the ostomy closure of FIG. 54 beginning to engage a pouch flange;

FIG. 62 is a view similar to FIG. 61 illustrating the ostomy closure in the process of engaging, the pouch flange;

FIG. 63 is a view similar to FIG. 62, illustrating the ostomy closure frilly engaged with the pouch flange;

FIG. 71 is a view of the ostomy closure of FIG. 64 beginning to engage the pouch flange;

FIG. 72 is a view similar to FIG. 71 illustrating the ostomy closure in the process of engaging the pouch flange;

FIG. 73 is a view similar to FIG. 72 illustrating the ostomy closure fully engage with the pouch flange;

FIG. 79 is a sectional view of FIG. 76;

FIG. 80 is an enlarged portion of FIG. 79;

FIG. 81 is a view of the ostomy closure of FIG. 74 beginning to engage a pouch flange;

FIG. 82 is a view similar to FIG. 81 illustrating the ostomy closure in the process of engaging; the pouch flange;

FIG. 82A is an enlarged portion of FIG. 82;

FIG. 83 is a view similar to FIG. 82 illustrating the ostomy closure fully engaged with the pouch flange;

FIG. 83A is an enlarged portion of FIG. 83;

FIG. 89 is a sectional view of FIG. 86;

FIG. 90 is an enlarged portion of FIG. 89;

FIG. 91 is a view of the ostomy closure of FIG. 84 beginning to engage a pouch flange;

FIG. 92 is a view similar to FIG. 91 illustrating the ostomy closure in the process of engaging the pouch flange;

FIG. 93 is a view similar to FIG. 92 illustrating the ostomy closure fully engaged with the pouch flange.

Similar reference characters refer to similar parts throughout the several Figures of the drawings.

DETAILED DESCRIPTION

Figure 2:
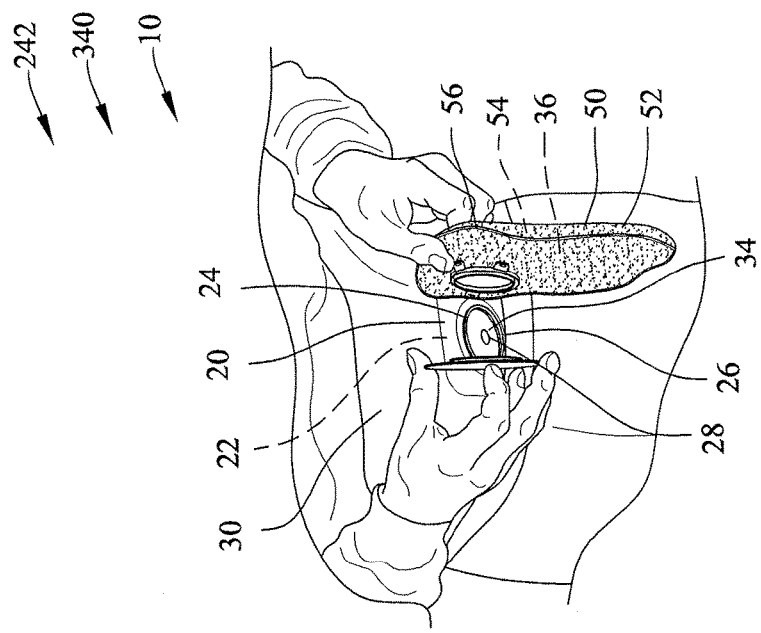
FIG. 2 is an enlarged portion of FIG. 1, illustrating the ostomy pouch removed from are ostomy mounting, plate and a first embodiment for an ostomy closure incorporating the subject matter of the disclosure.
Figure 1:
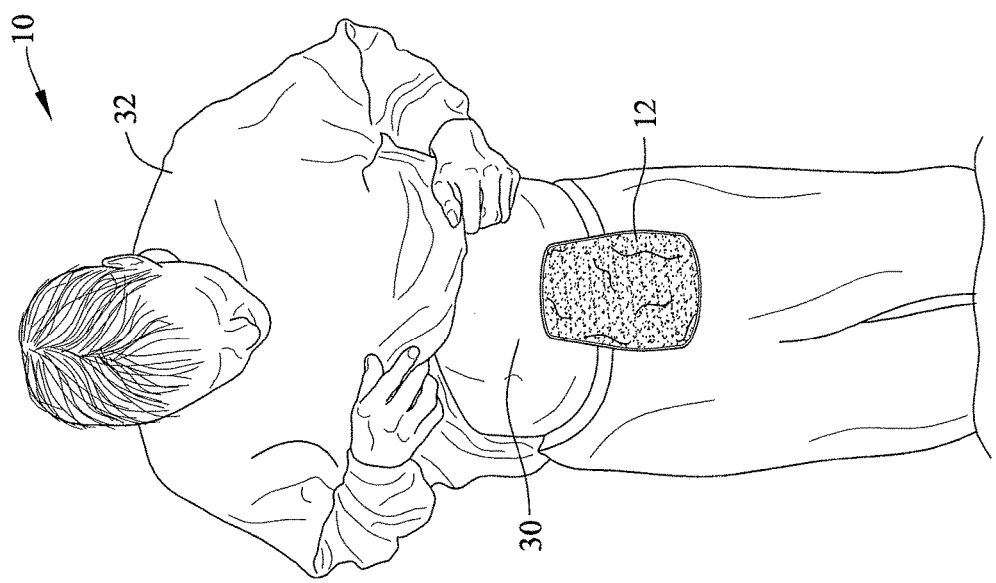
FIG. 1 is a front view of an individual having an ostomy pouch engaging an abdominal wall.
Figure 3:
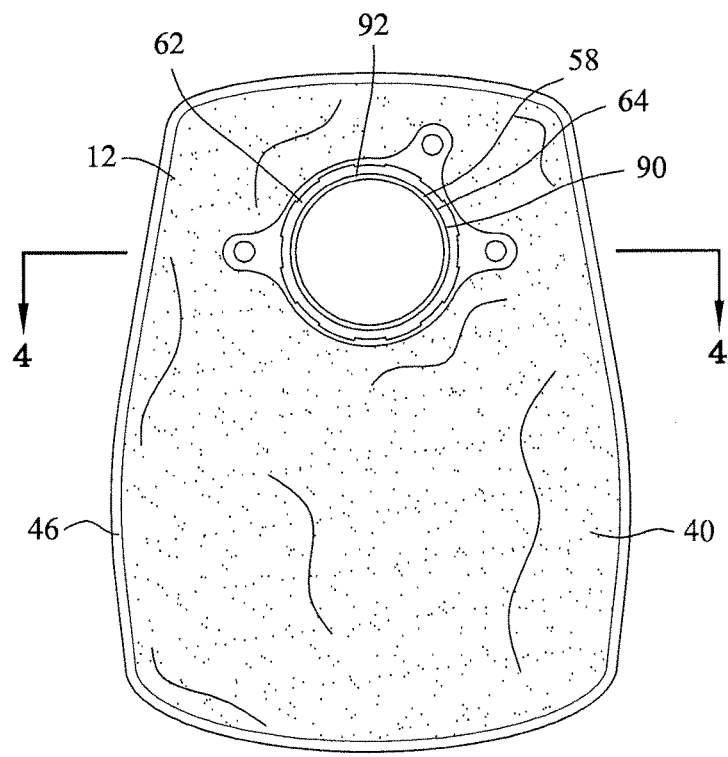
FIG. 3 is a front view of the ostomy pouch incorporating prior art.
Figure 4:
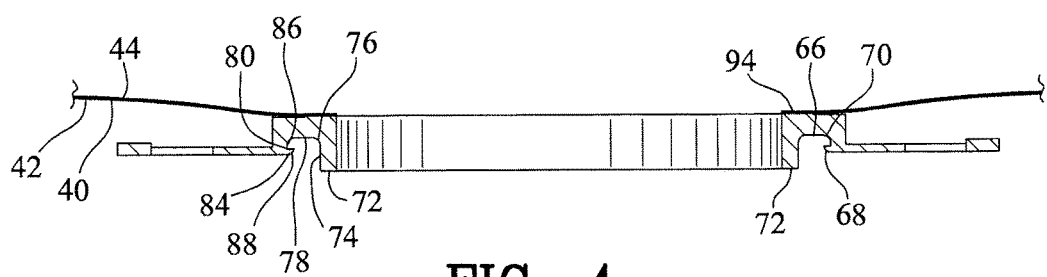
FIG. 4 is a sectional view along line 4-4 in FIG. 3 incorporating prior art.
Figure 5:
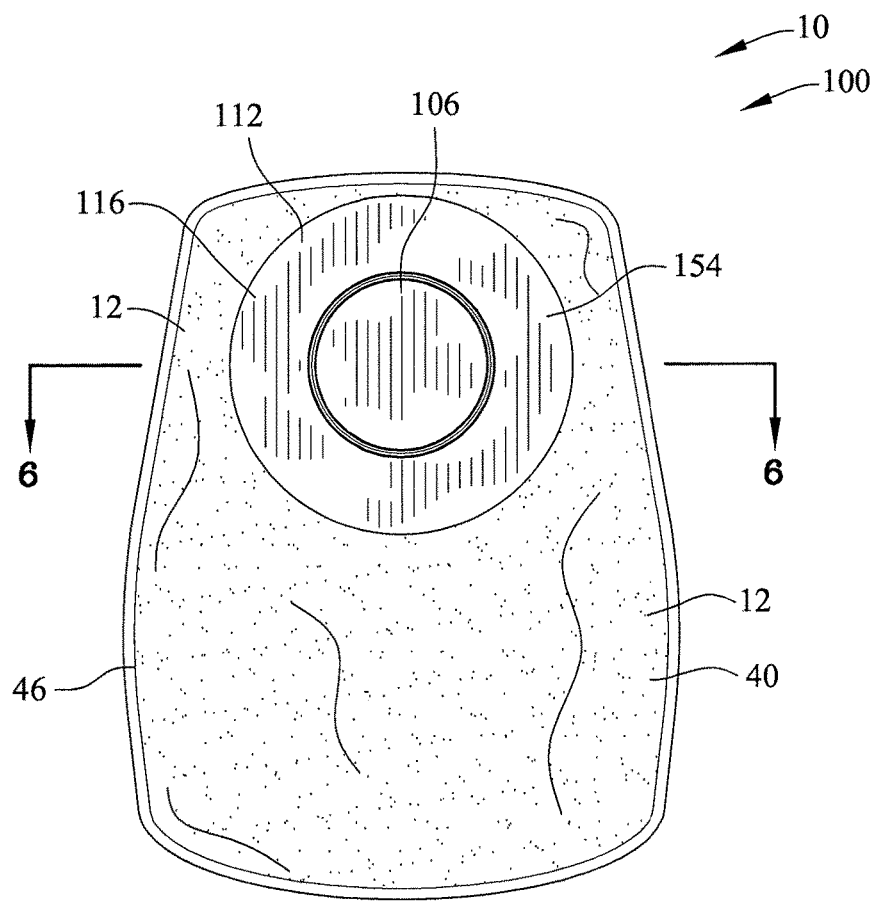
FIG. 5 is a view similar to FIG. 3 having the ostomy closure engaging the ostomy pouch.

FIGS. 1-53 are multiple embodiments for an ostomy closure 10 for sealing an ostomy pouch 12 after use and removal from an ostomy mounting plate 20. Both the ostomy pouch 12 and the ostomy mounting plate 20 constitute prior art. As best shown in FIGS. 1 and 2, the ostomy pouch 12 is coupled to the abdominal wall 30 of an individual 32 by the ostomy mounting plate 20. The ostomy mounting plate 20 is secured to an abdominal wall 30 of an individual 32 by an adhesive plate layer 22 The ostomy mounting plate 20 includes a plate flange 24. A plate locking member 26 is integral to the plate flange 24. A plate orifice 28 is positioned within the plate flange 24 and traverses the ostomy mounting plate 20. The plate orifice 28 is aligned with a stoma 34 located in the abdominal wall 30.

As shown in FIGS. 1-4, the ostomy pouch 12 has a first flexible layer 40 and a second flexible layer 50. The first flexible layer 40 includes an exterior surface 42 and an interior surface 44 extending to a first layer edge 46. The second flexible layer 50 includes an exterior surface 52 and an interior surface 54 extending to a second layer edge 56. The first layer edge 46 and—the second layer edge 56 are coupled by a heat sealing, gluing or other coupling means 94. The first layer edge 46 and the second layer edge 56 define an ostomy chamber 60. The first flexible layer 40 includes a pouch aperture 58 for access to the ostomy chamber 60. As shown in FIGS. 1-6, 26, 27, 40, 41 and 45-49, the ostomy pouch 12 may include a closed-end ostomy pouch 14.

A pouch flange 62 is securing to the exterior surface 42 of the first flexible layer 40. The pouch flange 62 includes a pouch orifice 64 wherein the pouch orifice 64 is aligned with the pouch aperture 58. The pouch flange 62 further includes a pouch sealing member 6 and a pouch locking member 68. The pouch sealing member 66 comprises a first generally J-shaped mating member 70. More specifically, the pouch sealing member 66 extends from a pouch seal rim 72 and surface 72, a first linear member and surface 74, a primary arcuate member and surface 76, a second linear member and surface 78, to a secondary arcuate member and surface 80. The pouch locking member 68 is integral to the pouch flange 62 and comprises a first locking tab 84 extending from the secondary arcuate member 80. More specifically, the first locking tab 84 extends from a main linear lock member 86 to a main arcuate lock member 88. The pouch flange 62 is shown to include a circular configuration 90 providing the first generally J-shaped mating member 70 and the pouch locking member 82 with an annular configuration 92.

As shown in FIGS. 1 and 2, the pouch flange 62 engages with the plate flange 24 and the pouch locking member 68 engages with the plate locking member 26 for coupling the ostomy pouch 12 to the plate flange 24 and for conveying stool 36 from the individual 32 to the ostomy chamber 60. The stool 36 releases a stool odor 38. The pouch flange 62 disengages with the plate flange 24 for dispose of the stool 36. Upon the removal of the ostomy pouch 12 from the ostomy mounting plate 20, the pouch orifice 64 is exposed where the stool 36 may escape from the ostomy pouch 12.

FIGS. 2-13 illustrate a first embodiment 100 of the ostomy closure 10 for maintaining the stool 36 and the stool odor 38 within the ostomy chamber 60. The first embodiment 100 of the ostomy closure 10 comprises a cap body 102 defining an interior surface 104 and an exterior surface 106 extending to a peripheral edge 108. A cap flange 110 is coupled to the peripheral edge 108 of the cap body 102 and extends from the interior surface 104 of the cap body 102. A cap lip 112 defining an interior surface 114 and an exterior surface 116 extend from the cap flange 110 for manipulating the cap body 102 and the cap flange 110.

The cap flange 110 further includes a cap sealing member 120 and a cap locking member 122. The cap sealing member 120 comprises a second generally J-shaped mating member 124. More specifically, the cap sealing member 120 extends from the interior surface 104 of the cap body 102, a third linear member and surface 126, a major arcuate member and surface 128, a fourth linear member and surface 130, to a minor arcuate member and surface 132. The cap locking member 122 is integral to the cap flange 110 and comprises a second locking tab 134 extending from the minor arcuate member 132. More specifically, the second locking tab 134 extends from a minor linear lock member 136 to a minor arcuate lock member 138. The cap flange 110 is shown to include a circular configuration 140 providing the second generally J-shaped mating member 124 and the cap locking member 122 with an annular configuration 142.

Figure 6:
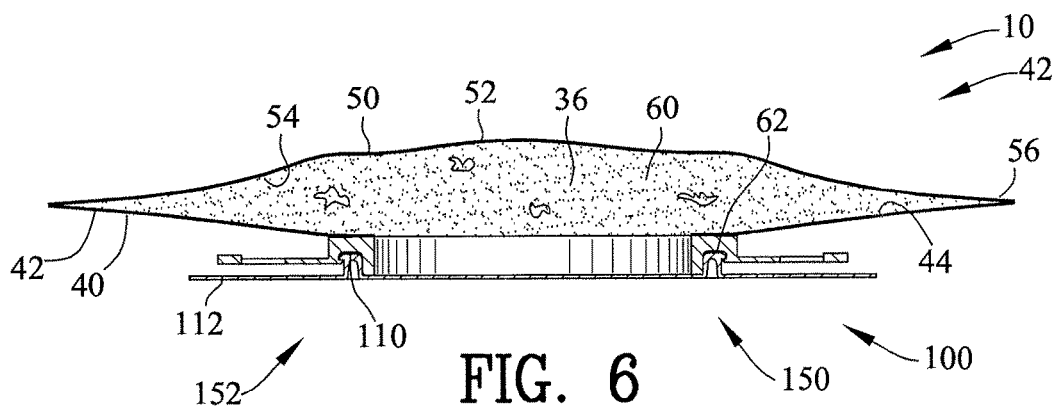
FIG. 6 is a sectional view along line 6-6 in FIG. 5.
Figure 7:
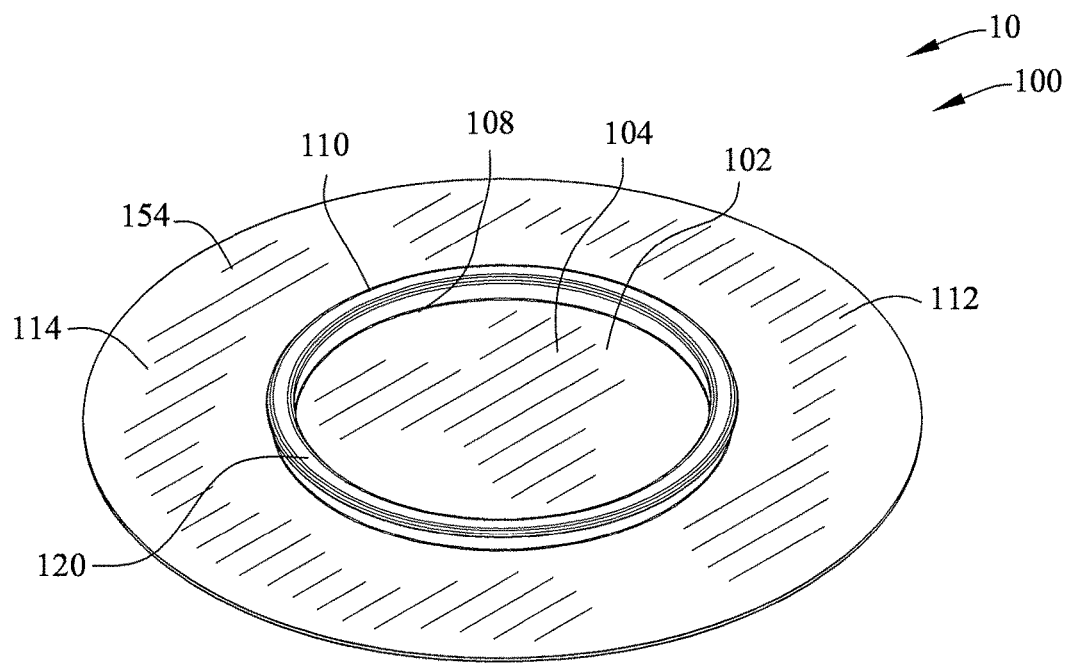
FIG. 7 is a top isometric view of the ostomy closure of FIGS. 2 and 5.
Figure 8:
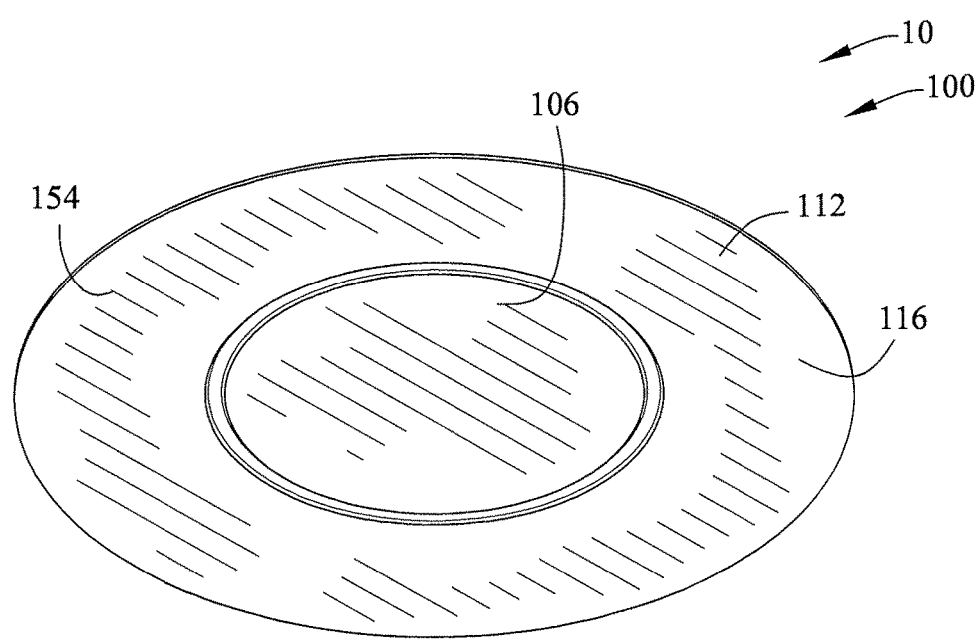
FIG. 8 is a bottom isometric view of FIG. 7.
Figure 9:
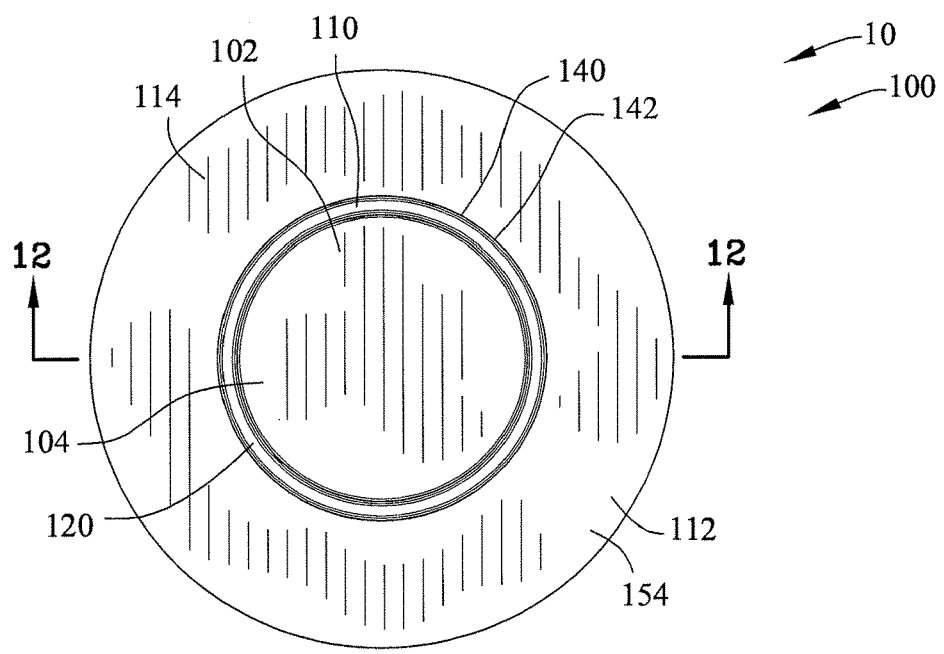
FIG. 9 is a top view of FIG. 7.
Figure 10:
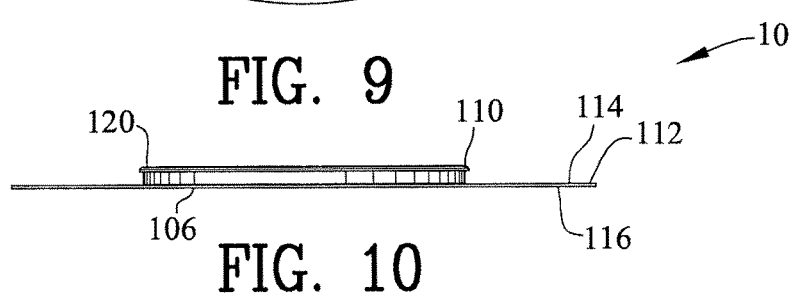
FIG. 10 is a side view of FIG. 9.
Figure 11:
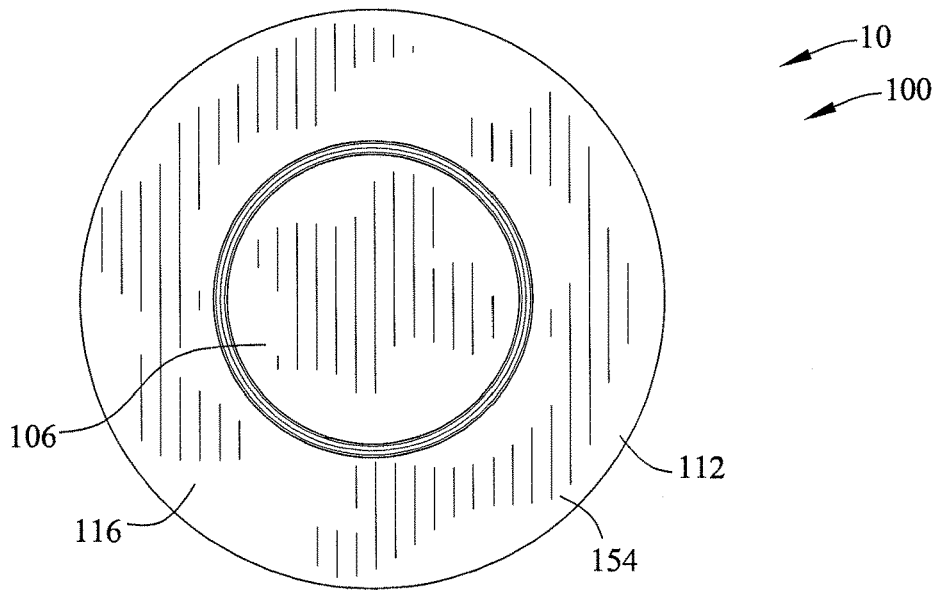
FIG. 11 is a bottom view of FIG. 9.
Figure 12:
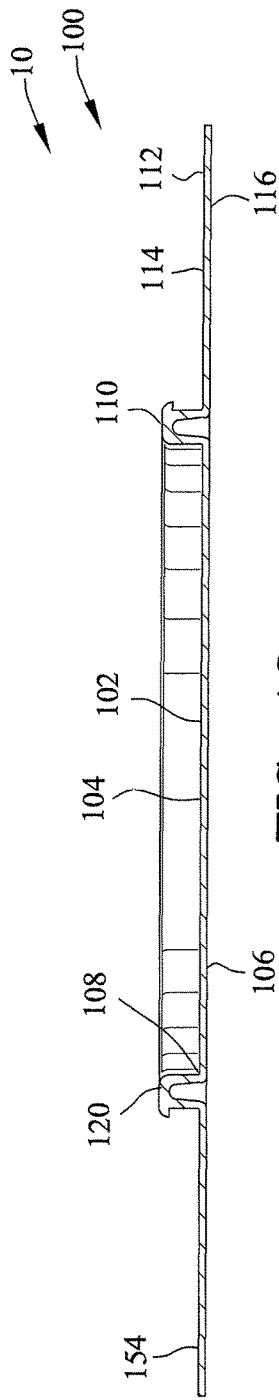
FIG. 12 is a sectional view along line 12-12 in FIG. 9.
Figure 13:
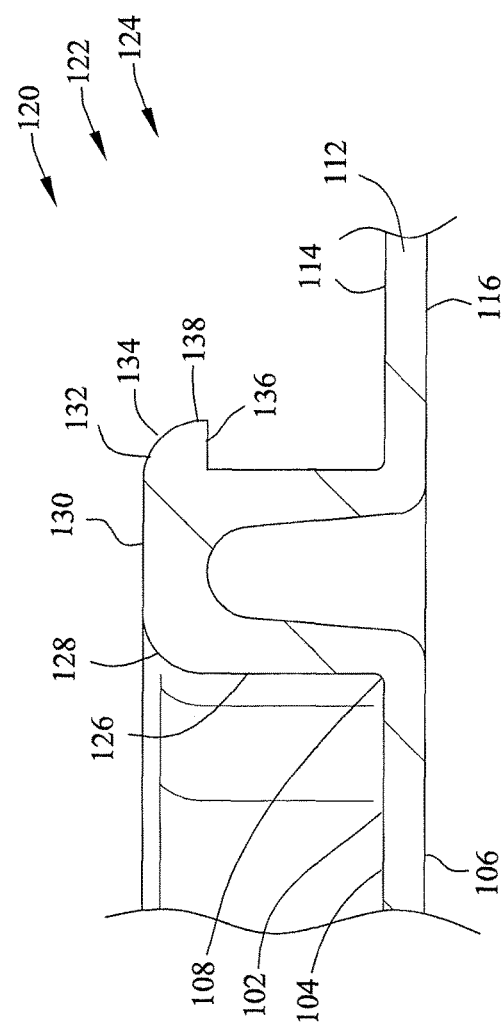
FIG. 13 is an enlarged portion of FIG. 12.
Figure 17:
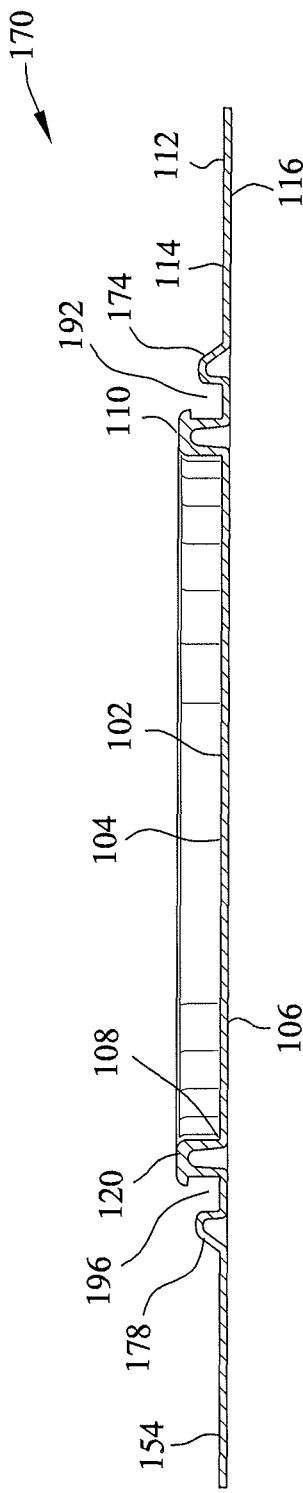
FIG. 17 is a sectional view along line 17-17 in FIG. 14.
Figure 18:
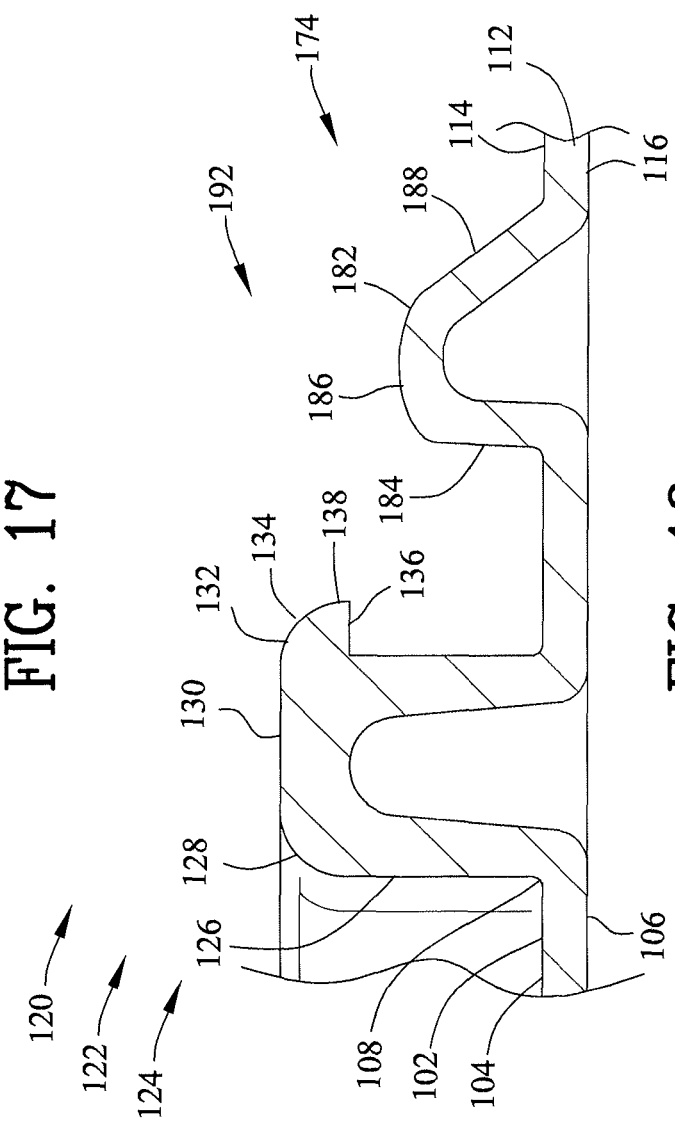
FIG. 18 is an enlarged portion of FIG. 17.
Figure 22:
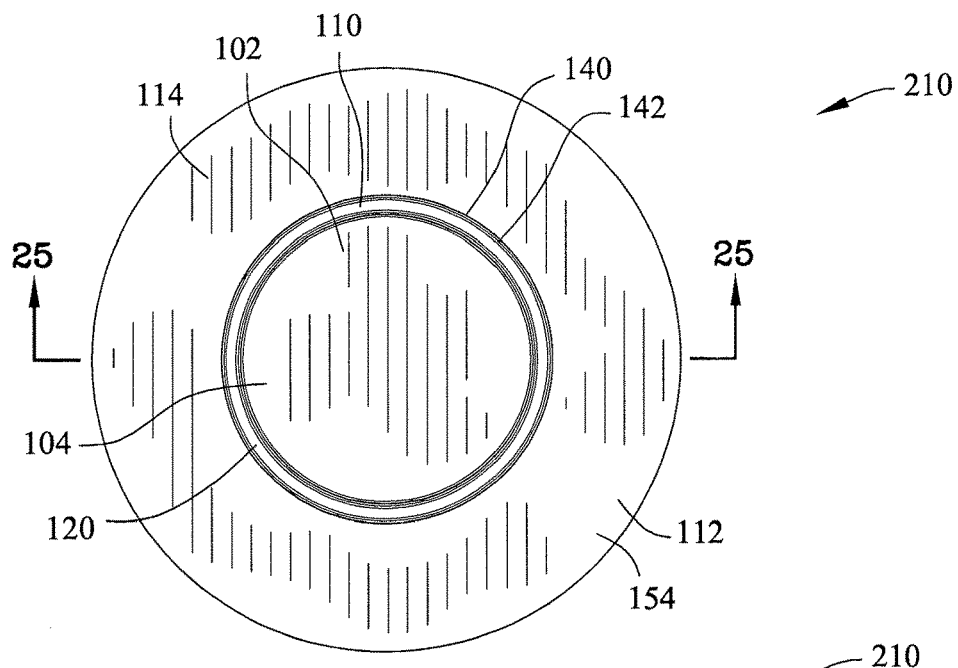
FIG. 22 is a top view of a third embodiment for an ostomy closure including a cap adhesive layer for temporarily seeming the ostomy closure to the ostomy pouch.
Figure 23:
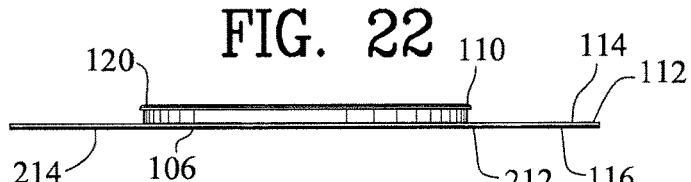
FIG. 23 is a side view of FIG. 22.
Figure 24:
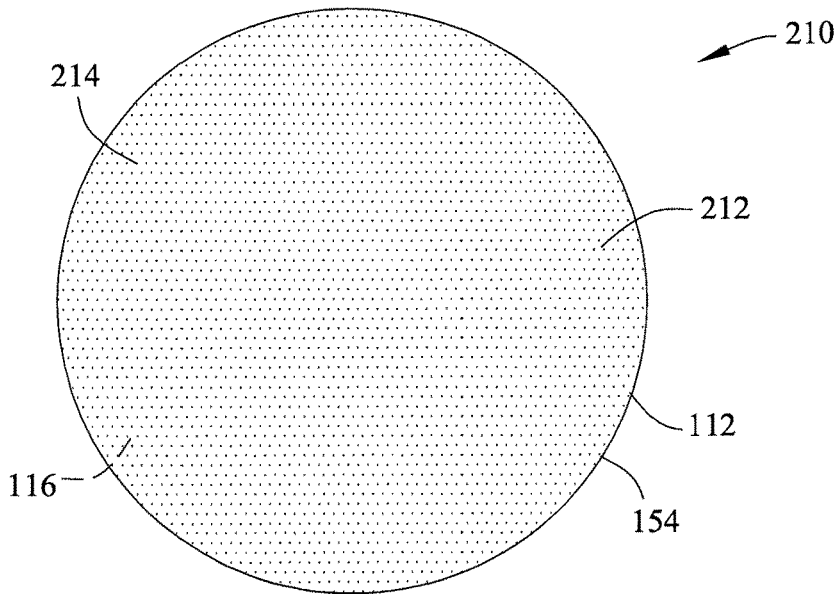
FIG. 24 is a bottom view of FIG. 22.
Figure 25:
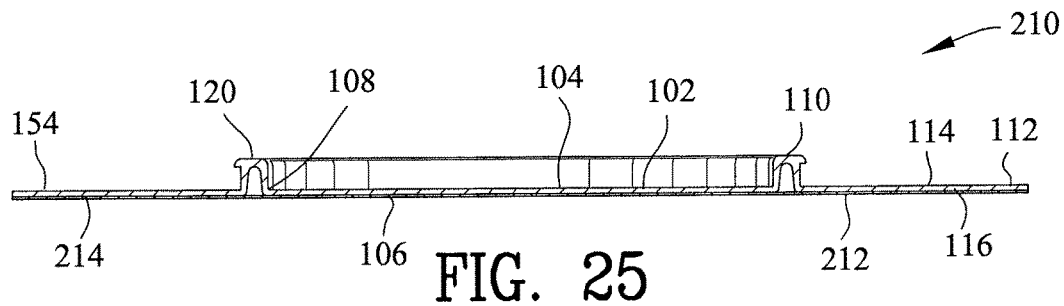
FIG. 25 is a sectional view along line 25-25 in FIG. 22.
Figure 26:
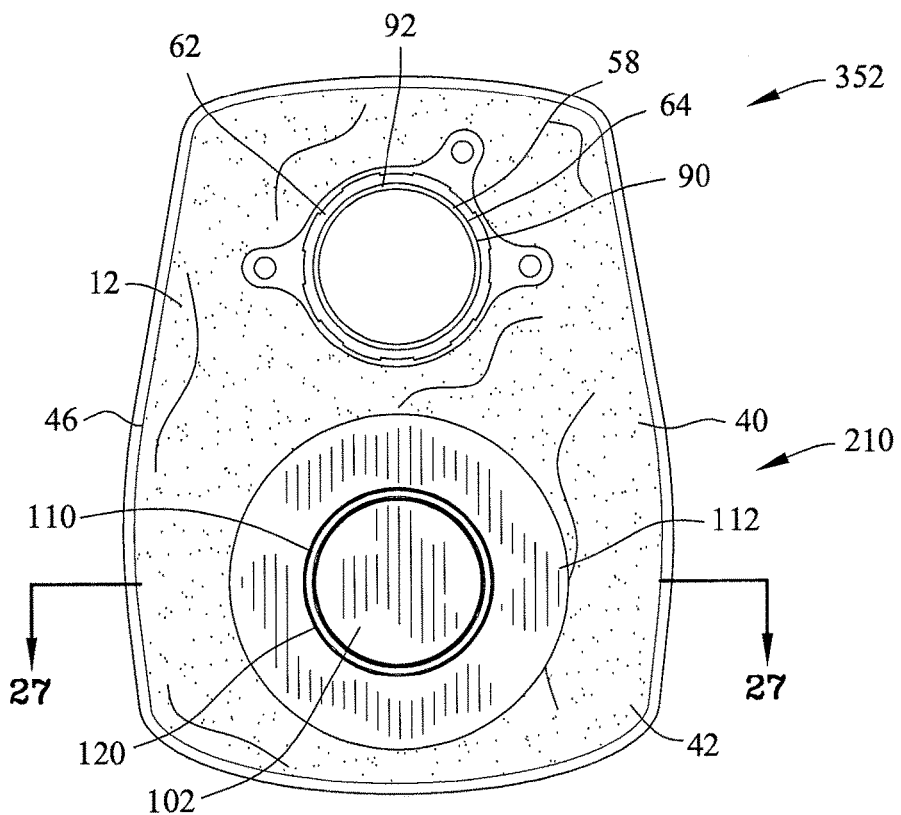
FIG. 26 is a view similar to FIG. 3 illustrating the ostomy closure of FIG. 22 wherein the cap adhesive layer temporarily securing the ostomy closure to the ostomy pouch.
Figure 27:
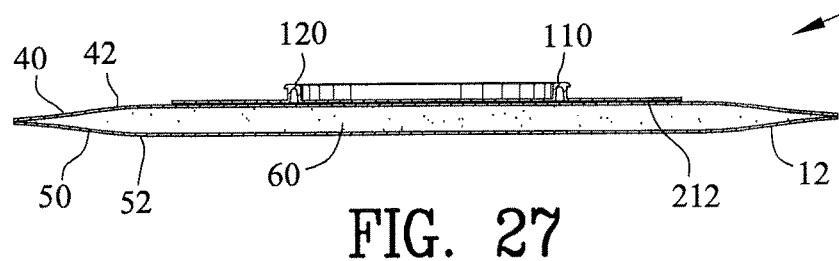
FIG. 27 is a sectional view along line 27-27 in FIG. 26.
Figure 28:
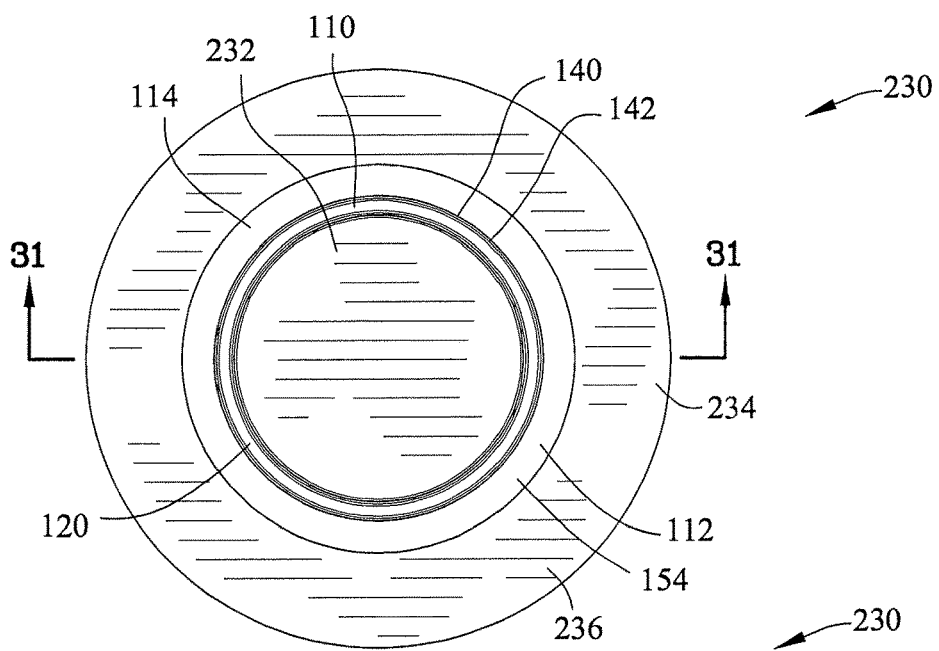
FIG. 28 is a top view of a fourth embodiment for an ostomy closure including a flexible sheet coupled to the cap flange for covering a cap flange aperture.
Figure 29:
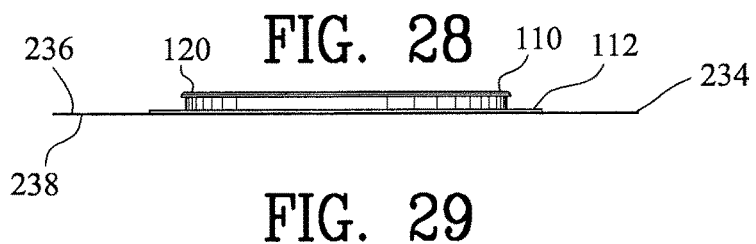
FIG. 29 is a side view of FIG. 28.
Figure 30:
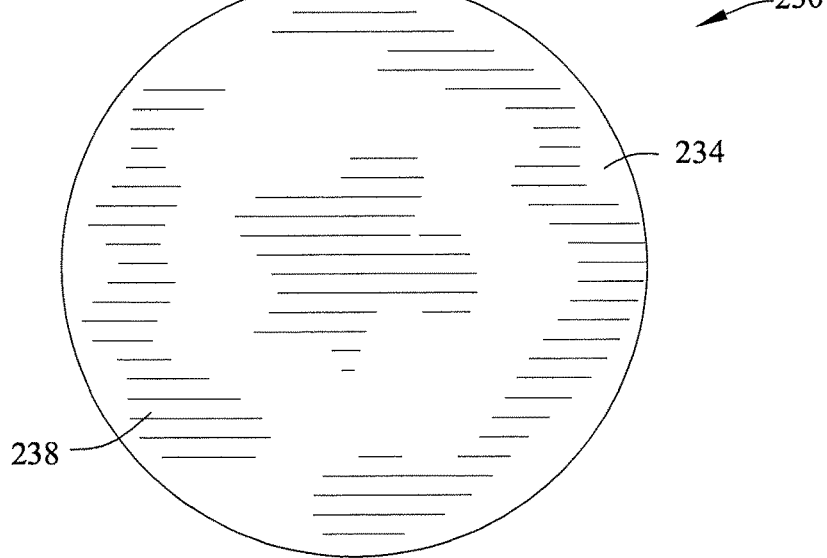
FIG. 30 is a bottom view of FIG. 28.
Figure 36:
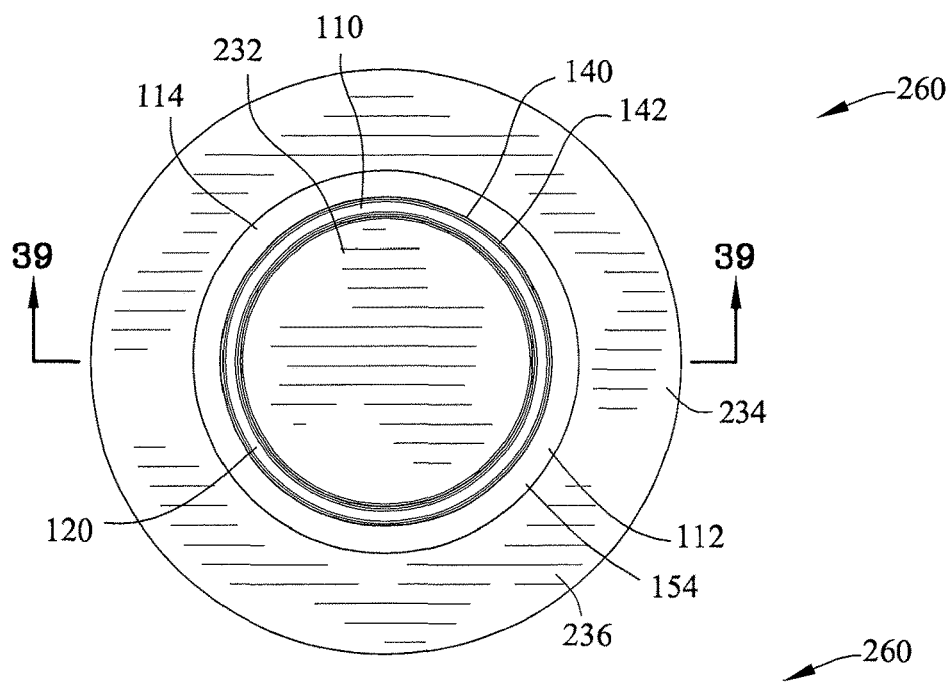
FIG. 36 is a top view of a sixth embodiment for an ostomy closure including an flexible sheet coupled to the cap flange for covering the cap flange aperture and a cap adhesive layer for temporarily securing the ostomy closure to the ostomy pouch.
Figure 37:
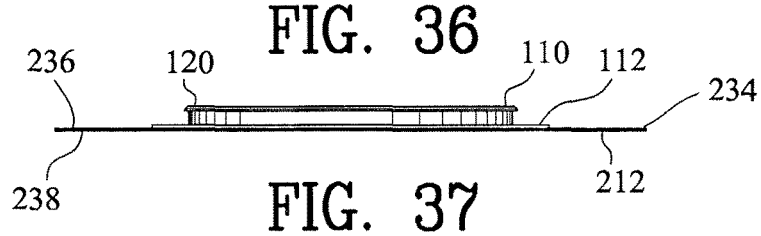
FIG. 37 is a side view of FIG. 36.
Figure 38:
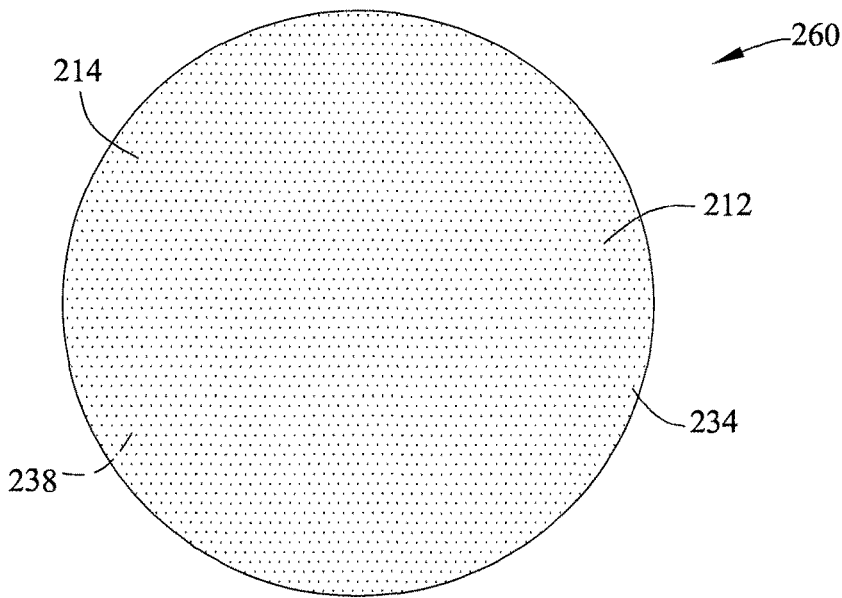
FIG. 38 is a bottom view of FIG. 36.
Figure 39:
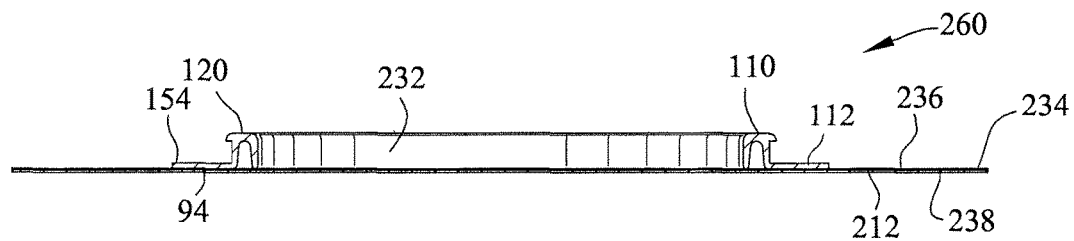
FIG. 39 is a sectional view along line 39-39 in FIG. 36.
Figure 40:
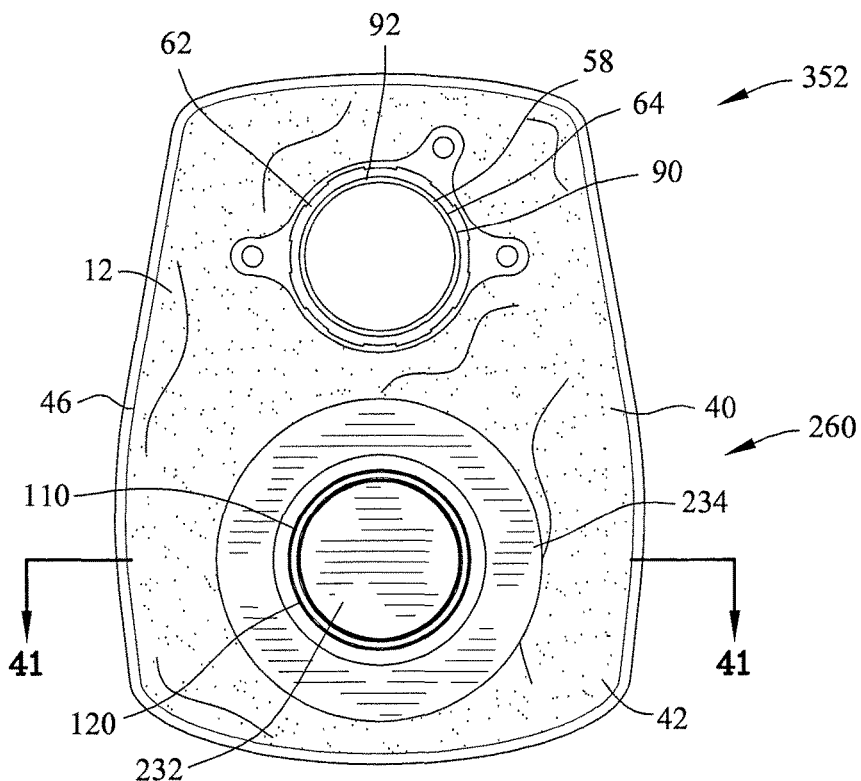
FIG. 40 is a view similar to FIG. 3 illustrating the ostomy closure of FIG. 36 wherein a cap adhesive layer temporarily securing the ostomy closure to the ostomy pouch.
Figure 41:
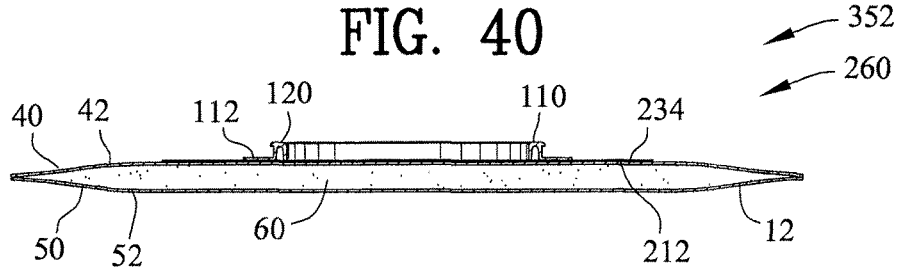
FIG. 41 is a sectional view along line 41-41 in FIG. 40.
Figure 42:
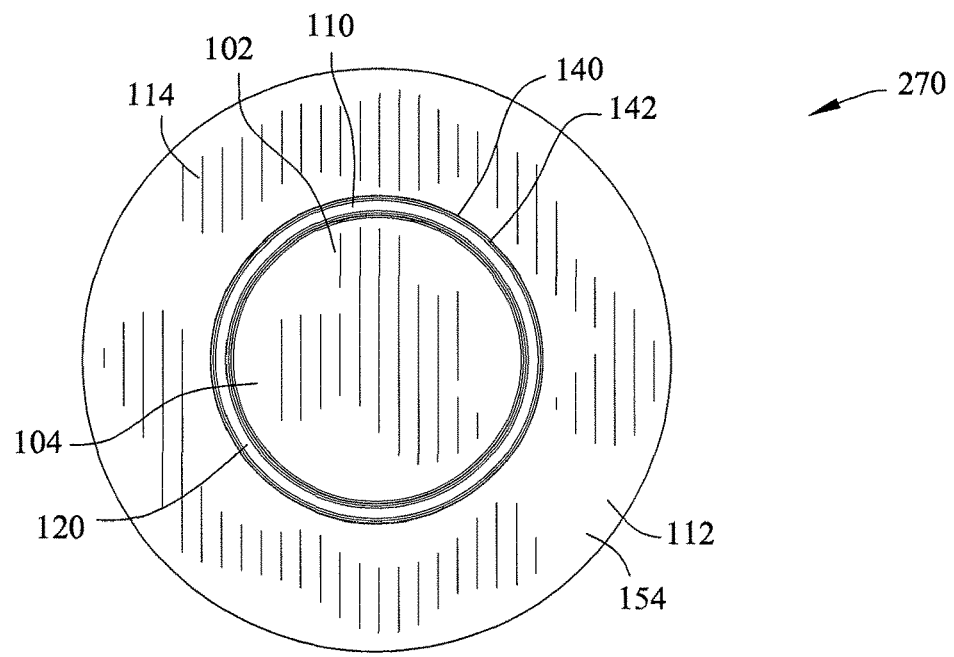
FIG. 42 is a top view of a seventh embodiment for an ostomy closure including a flexible storage mg coupled to the ostomy closure.

As shown in FIG. 6, the cap flange 110 couples with the pouch flange 62 for positioning the cap body 102 over the pouch orifice 64 and defining a sealing closure 150. More specifically, the pouch seal rim 72 and surface 72, the first linear member and surface 74, the primary arcuate member and surface 76, the second linear member and surface 78, and the secondary arcuate member and surface 80 of the pouch sealing member 66 seat against the interior surface 104 of the cap body 102, a third linear member and surface 126, a major arcuate member and surface 128, a fourth linear member and surface 130, to a minor arcuate member and surface 132 of the cap sealing member 120 respectively. The sealing closure 150 maintains the stool 36 and the stool odor 38 within the ostomy chamber 60.

Upon the cap flange 110 fully coupling with the pouch flange 62, the cap locking member 122 engages with the pouch locking member 68 for defining a locking closure 152. More specifically, the main linear lock member 86 and the main arcuate lock member 88 of the first locking tab 84 locks against the minor linear lock member 136 and the minor arcuate lock member 138 of the second locking tab 134 respectively. The locking closure 152 prevents inadvertent removal of the cap flange 110 from the pouch flange fit. Preferably, the cap body the flange 110 and the cap lip 112 define a unitary-one-piece unit 154 constructed from injected molding process.

FIGS. 14-21 illustrate a second embodiment 170 of the ostomy closure 10 for maintaining the stool 36 and the stool odor 38 within the ostomy chamber 60. The second embodiment 170 of the ostomy closure 10 includes the interior surface 114 of the cap lip 112 including a first aligning tab 172, a second aligning tab 174, a third aligning tab 176 and a four aligning tab 178 positioning adjacent to the cap flange 110. Preferably, the first aligning tab 172, the second aligning tab 174, the third aligning tab 176 and the four aligning tab 178 defining an equidistance orientation 180 about the cap flange 110. Each of the first, second, third and fourth aligning tabs 172, 174, 176 and 178 include a generally J-shaped aligning member 182. More specifically, the first, second, third and fourth aligning tabs 172, 174, 176 including a first linear aligning member and surface 184 extending perpendicularly from the interior surface 114 of the cap lip 112, an aligning arcuate member and surface 186 and a second linear aligning member and surface 188 extending non-perpendicularly from the interior surface 114 of the cap lip 112.

The first aligning tab 172, the second aligning tab 174, the third aligning tab 176 and the four aligning tab 178 and the cap flange 110 define a first aligning channel 190, a second aligning channel 192, a third aligning channel 194 and a fourth aligning channel 196 respectively for centering the cap flange 110 relative to the pouch flange 62 prior to the cap flange 110 coupling within the pouch flange 62. More specifically, the pouch flange 62 is inserted into the first aligning channel 190, the second aligning channel 192, the third aligning channel 194 and/or the fourth aligning channel 196 to facilitate the alignment between the cap flange 110 and the pouch flange 62 and expedite the sealing closure 150 and locking closure 152. Preferably, the cap body 102, the cap flange 110 and the cap lip 112 define a unitary-one-piece unit 154 constructed from injected molding process.

FIGS. 22-27 illustrate a third embodiment 210 of the ostomy closure 10 for maintaining the stool 36 and the stool odor 38 within the ostomy chamber 60. The third embodiment 210 of the ostomy closure 10 includes the exterior surface 106 of the cap body 102 having a cap adhesive layer 212 for temporarily securing the cap body 102 to the ostomy pouch 12. Furthermore, the exterior surface 116 of the cap lip 112 may have a second cap adhesive layer 214 for temporarily securing the cap body 102 to the ostomy pouch 12. The first and second cap adhesive layer 212 and 214 may be utilized for positioning the cap body 102 to the exterior surface 42 of the first flexible layer 40 while the ostomy pouch 12 is engaged with the plate flange 24. After the ostomy pouch 12 is disengaged from the plate flange 24, the individual 32 may promptly remove the cap body 102 from the ostomy pouch 12 for engaging the cap body 102 with the pouch flange 62.

FIGS. 28-32 illustrate a fourth embodiment 230 of the ostomy closure 10 for maintaining the stool 36 and the stool odor 38 within the ostomy chamber 60. The fourth embodiment 230 of the ostomy closure 10 includes the cap flange 110 defining a cap flange aperture 232. A flexible sheet 234 defines an interior surface 236 and an exterior surface 238. The interior surface 236 of the flexible sheet 234 is coupled to the cap flange 110 for covering the cap flange aperture 232. The cap flange 110 couples with the pouch flange 62 for positioning the flexible sheet 234 over the pouch orifice 64 and defining the sealing closure 150. The sealing closure 150 maintains the stool 36 and the stool odor 38 within the ostomy chamber 60. The cap locking member 122 engages with the pouch locking member 68 for defining a locking closure 152. The locking closure 152 prevents inadvertent removal of the cap flange 110 from the pouch flange 62. Preferably, the cap flange 62 and the cap lip 112 defining a unitary-one-piece unit 154 constructed from injected molding process. The cap flange 62 and the flexible sheet 234 may be coupled by a heat sealing, gluing or other coupling means 94.

FIGS. 33-35 illustrate a fifth embodiment 250 of the ostomy closure 10 for maintaining the stool 36 and the stool odor 38 within the ostomy chamber 60. The fifth embodiment 250 of the ostomy closure 10 combines the second embodiment 170 in FIGS. 14-21 with the fourth embodiment 230 of FIGS. 28-32.

FIGS. 36-41 illustrate a sixth embodiment 260 of the ostomy closure 10 for maintaining the stool 36 and the stool odor 38 within the ostomy chamber 60. The sixth embodiment 260 of the ostomy closure 10 combines the third embodiment 210 of FIGS. 22-27 with the fourth embodiment 230 of FIGS. 28-32.

FIGS. 42-49 illustrate a seventh embodiment 270 of the ostomy closure 10 for maintaining the stool 36 and the stool odor 38 within the ostomy chamber 60. The seventh embodiment 270 of the ostomy closure 10 depicts a flexible storage bag 272. In some embodiments the flexible storage bag 272 may have an enclosure body 274 extending between a bag base 267 and a bag opening 278 as shown in FIG. 46. Enclosure body 274 may define a bag chamber 280. Flexible storage bag 272 may be constructed of a polymeric material or any other appropriate material that maintains stool 36 and stool odor 38 within the flexible storage bag 272.

Figure 43:
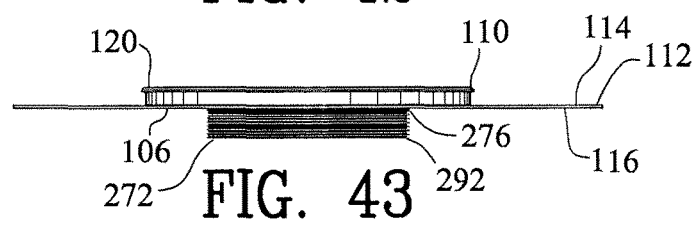
FIG. 43 is a side view of FIG. 42.
Figure 44:
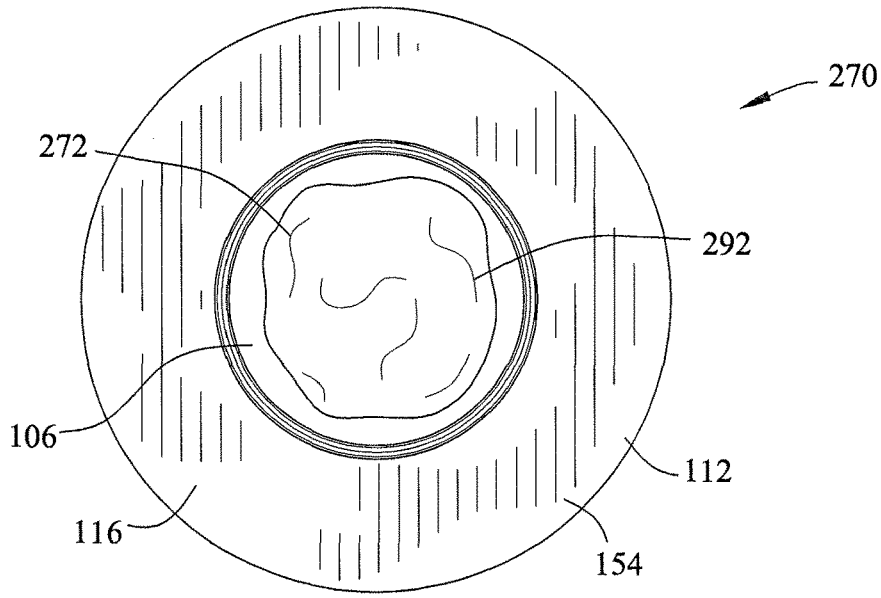
FIG. 44 is a bottom view of FIG. 42.
Figure 54:
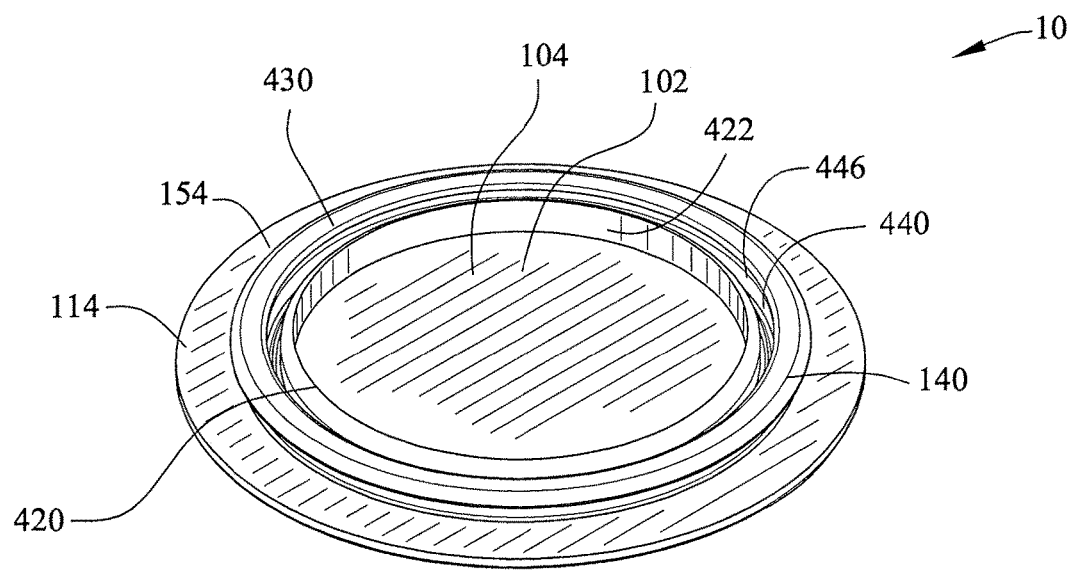
FIG. 54 is an isometric interior view of an additional embodiment for the ostomy closure.
Figure 55:
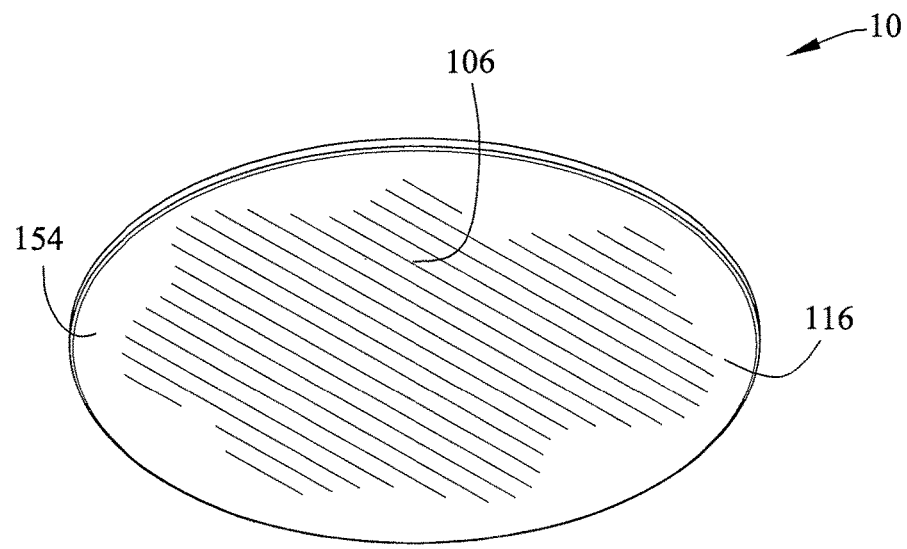
FIG. 55 is an isometric exterior view of FIG. 54.
Figure 56:
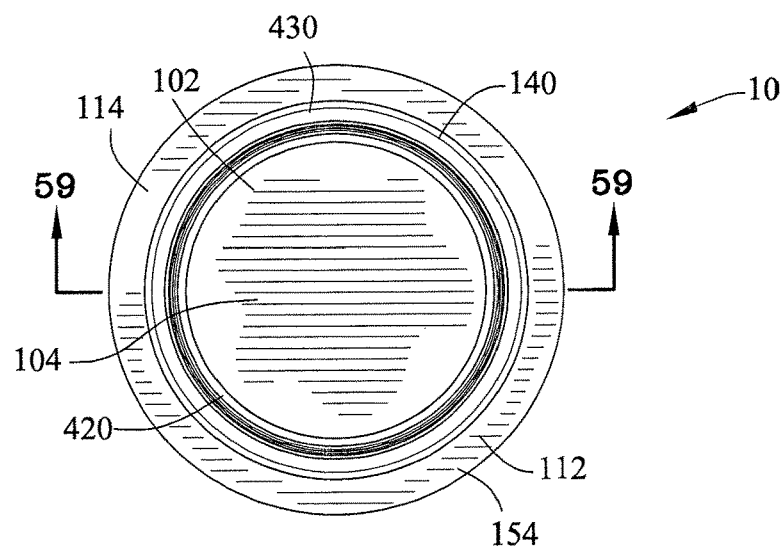
FIG. 56 is a top view of FIG. 54.
Figure 57:
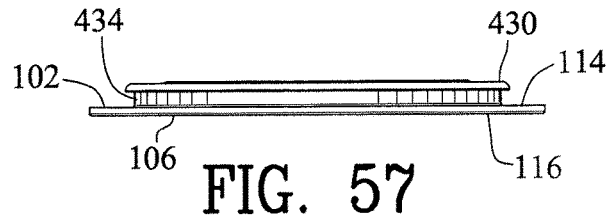
FIG. 57 is a side view of FIG. 56.
Figure 58:
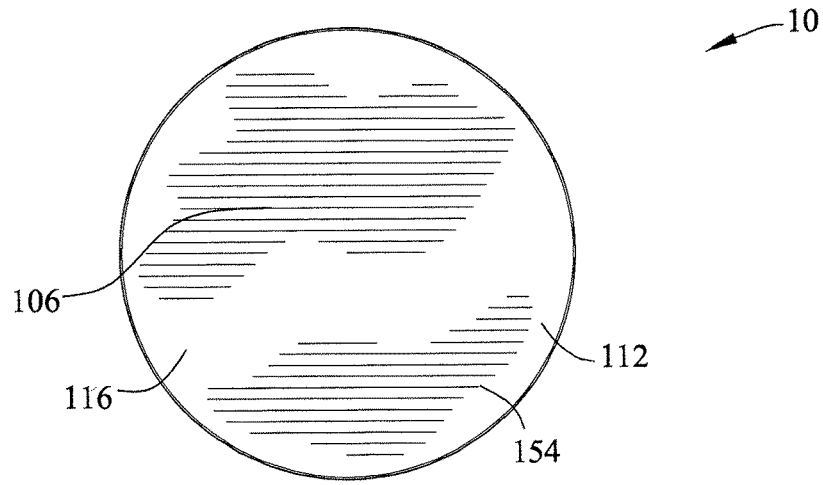
FIG. 58 is a bottom view of FIG. 56.
Figure 64:
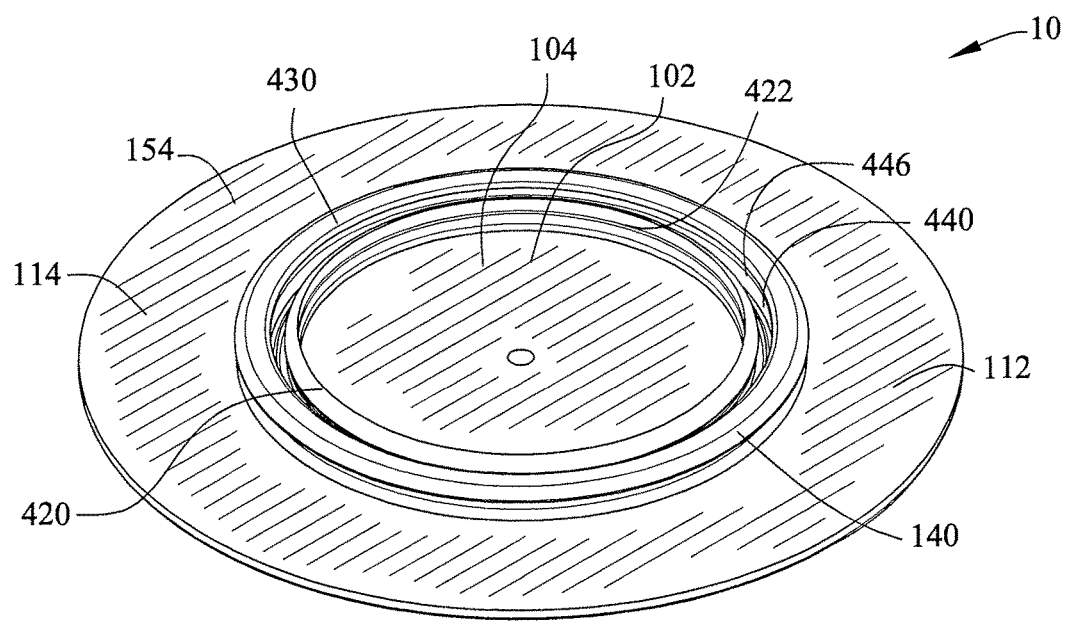
FIG. 64 is an isometric interior view of an additional embodiment for the ostomy closure.
Figure 65:
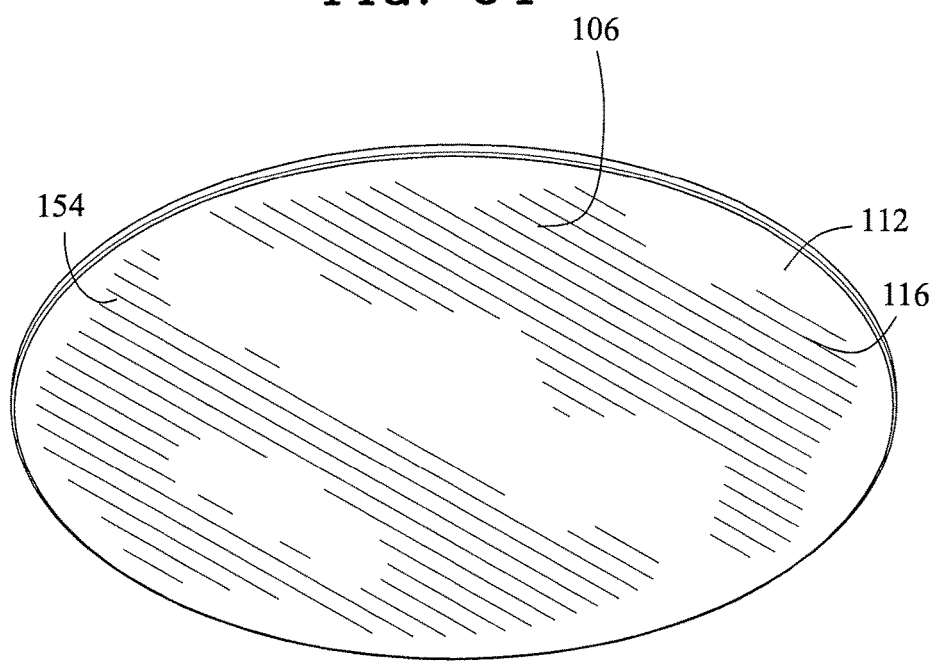
FIG. 65 is an isometric exterior view of FIG. 64.
Figure 66:
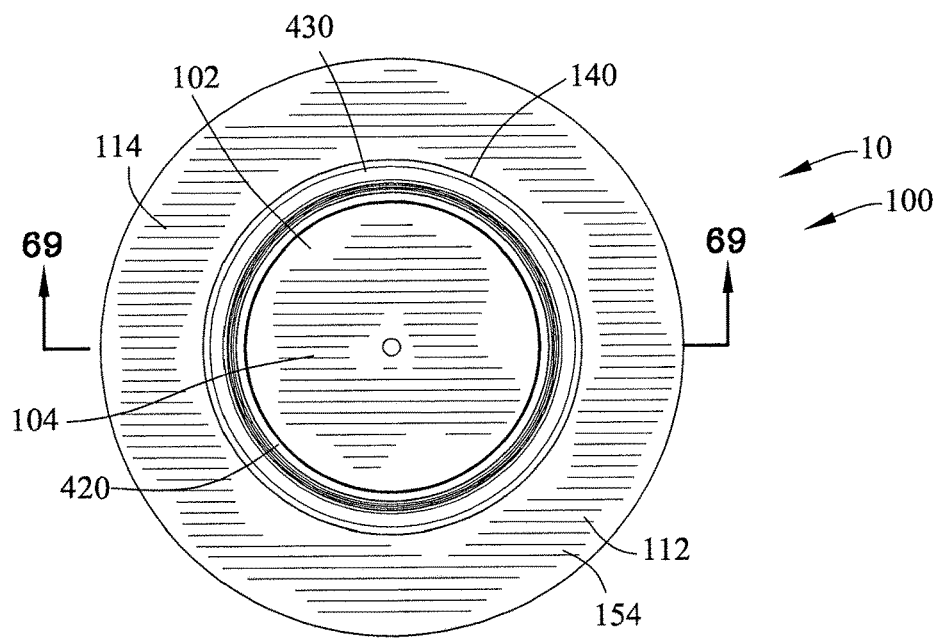
FIG. 66 is a top view of FIG. 64.
Figure 67:
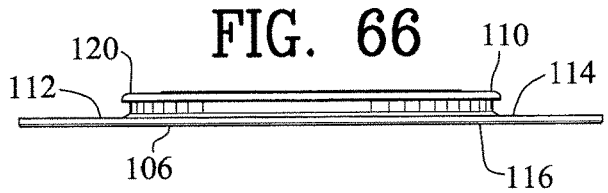
FIG. 67 is a side view of FIG. 66.
Figure 68:
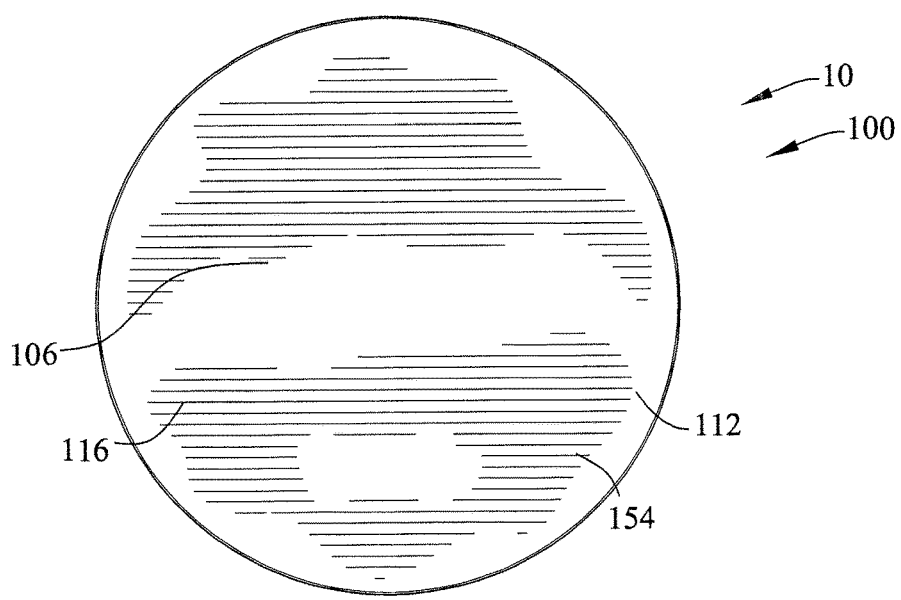
FIG. 68 is a bottom view of FIG. 66.
Figure 69:
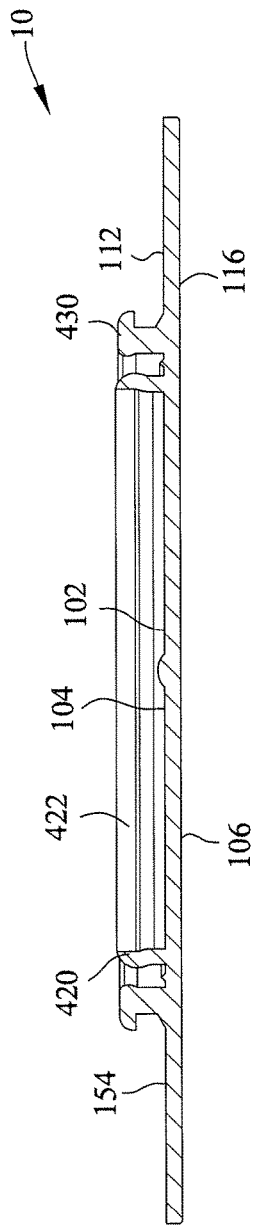
FIG. 69 is a sectional view of FIG. 66.

Bag base 276 may be coupled to exterior surface 106 of cap body 102 as shown in the first embodiment of FIGS. 2-13 or to exterior surface 238 of flexible sheet 234 as shown in the fourth embodiment of FIGS. 28-32. Flexible sheet 234 and cap flange 110 may define a cap and bag unit 290. As shown in FIGS. 43 and 45 enclosure body 274 may be compacted by folding, vacuum forming or other means on exterior surface 106 or exterior surface 238 for defining a temporary compact cap and bag unit 292. As shown in FIG. 46 enclosure body 274 may be subsequently expanded from exterior surface 106 or exterior surface 238 for defining a deployed cap and bag unit 294. As shown in FIG. 47 bag opening 278 may be retracted over the flexible storage bag 272 for defining an inverted flexible storage bag 296. As shown in FIG. 48 upon further retraction of flexible storage bag 272, bag opening 278 may be retracted over cap flange 110 for defining a bag cap enclosure 298. FIG. 48 also illustrates bag opening 278 retracting over ostomy pouch 12 for defining a bag pouch enclosure 300. As shown in FIG. 49 embodiments of a bag closure 302 may engage enclosure body 274 for encapsulating both cap flange 110 and ostomy pouch 12 within bag chamber 280. In some embodiments bag closure 302 may include a drawstring closure, knot, zip lock, adhesive or other fastening means. Accordingly flexible storage bag 272 may maintain stool 36 and stool odor 38 within bag chamber 280 if the cap sealing member 120 is inadvertently ruptured.

FIGS. 50-53 illustrate an eighth embodiment 318 of the ostomy closure 10 for maintaining the stool 36 and the stool odor 38 within the ostomy chamber 60. The eighth embodiment 318 of the ostomy closure 10 includes a sheet of ostomy closures 320 for sealing a plurality of ostomy pouches 12. The sheet of ostomy closures 320 comprises a plurality of cap bodies 102 defining an interior surface 104 and an exterior surface 106 extending to a peripheral edge 108. The plurality of cap flanges 110 are coupled to the peripheral edge 108 of the plurality of cap bodies 102 and extend from the interior surface 104 of the plurality of cap bodies 102. The plurality of cap locking members 122 are integral to the plurality of cap flanges 110. The plurality of cap lips 112 define an interior surface 114 and an exterior surface 116 extending from the plurality of cap flanges 110 for manipulating the plurality of cap bodies 102 and the plurality of cap flanges 110.

A perforated edge 324 traverse the plurality of cap bodies 102 for assisting in the separation of each of the plurality of cap bodies 102. Each of the plurality of cap flanges 110 couple with the pouch flange 62 for positioning each of the plurality of cap bodies 102 over the pouch orifice 64 and define a sealing closure 150. The sealing closure 150 maintains the stool 36 and the stool odor 38 within the ostomy chamber 60. Each of the plurality of cap locking members 122 engage with the pouch locking member 68 for defining a locking closure 152. The locking closure 152 prevents inadvertent removal of the plurality of cap flanges 110 from the pouch flange 62.

As shown in FIG. 53, the exterior surface I 06 of the plurality of cap bodies 102 may include the cap adhesive layer 212 for temporarily securing each of the plurality of cap bodies 102 to the ostomy pouch 12. An adhesive backing sheet 322 is secured to the cap adhesive layer 212 for protecting and preventing; unwanted adhesion to the cap adhesive layer 212. The sheet of ostomy closures 320 may further include a plurality of flexible storage bags 272 as shown in FIGS. 42-49 for the seventh embodiment 270 engaging each of either the plurality of cap bodies 102 or the plurality of flexible sheets 234.

The subject matter of the disclosure further incorporates a method for utilizing an ostomy closure 10 for sealing an ostomy pouch 12. The method comprising the steps of first disengaging 340 the pouch locking member 68 from the plate locking member 26 as shown in FIG. 2. A further step includes disengaging 342 the pouch flange 62 from the plate flange 24 as shown in FIG. 2.

The method may further include the step of removing 352 the cap body 102 from the ostomy pouch 12 that is temporarily secured by the cap adhesive layer 212 as shown in FIGS. 26, 27, 40 and 41. FIGS. 19 and 20 illustrate a possible further step wherein the individual 32 centers 350 the aligning channel 190 relative to the cap flange 110 for centering the cap flange 110 relative to the pouch flange 62 prior to the cap flange 110 coupling within the pouch flange 62. FIGS. 19-21 illustrate the step of engaging 344 the cap flange 110 with the pouch flange 62 for positioning a cap body 102 over the pouch orifice 64 and maintaining the stool 36 and the stool odor 38 within the ostomy chamber 60. A further step includes engaging the cap locking member 122 with the pouch locking member 68 as shown in FIGS. 20 and 21 for preventing inadvertent removal of the cap flange 110 from the pouch flange 62.

FIGS. 45 and 46 illustrate a possible further step wherein the flexible storage bag 272 is expanded 360 from either the cap body 102 or the flexible sheet 234. A further step includes retracting 362 the bag opening 278 of the flexible storage bag 272 over the flexible storage bag 272 as shown in FIG. 47. As shown in FIG. 48, the enclosure body 274 may be further retracted 364 in which the bag opening 278 traverses over the cap flange 110. As also illustrated in FIG. 48, the enclosure body 274 may be further retracted 366 in which the bag opening 278 traverses over the ostomy pouch 12. Thereafter, the method may include sealing 368 the flexible storage bag 272 for encapsulating both the cap flange 110 and the ostomy pouch 12 within the bag chamber 280 as shown in FIG. 49. The flexible storage bag 272 maintains the stool 36 and the stool odor 38 within the bag chamber 280 if the cap sealing member 120 is inadvertently ruptured.

FIGS. 54-63, 64-73, 74-83A and 84-93 include additional embodiments for a closure 10, which engages a pouch 12. A pouch 12 and closure 10 for deposing stool 36 from an individual 32.

The pouch 12 and closure 10 comprises an ostomy pouch 12 having a first flexible layer 40 coupling to a second flexible layer 50 for defining an ostomy chamber 60. A pouch flange 62 is secured to the first flexible layer 40. The pouch flange 62 as shown in FIGS. 54-63, 64-73, 74-83A and 84-93 may be similar to Hollister® or Convex®. The pouch flange 62 as shown in FIGS. 74-83A may be similar to Coloplast®.

A circular sealing wall 400 extends from the pouch flange 62 including an interior wall surface 402, an exterior wall surface 404 and a top wall surface 406. A circular locking channel 410 extends from the exterior wall surface 404 of the circular sealing wall 400. A cap body 102 defines an interior surface 104 and an exterior surface 106 extending; to a peripheral edge 108.

A circular sealing tab 420 extends from the interior surface 104 of the cap body 102 including an interior border surface 422, an exterior border surface 424 and a top border surface 426.

A circular locking leg 430 extends from the interior surface 104 of the cap body 102 including an interior leg surface 432, an exterior leg surface 434 and a top leg surface 436. A circular locking foot 438 extends from the external leg surface 434 of the circular locking leg 430.

The circular sealing tab 420 and the circular locking leg 430 define a circular cap channel 446 having a circular channel base 448. The circular locking leg 430 is positioned within the circular locking channel 440 for coupling the cap body 102 to the pouch flange 62 and for compressing the interior wall surface 402 of the circular sealing wall 400 against the exterior border surface 424 of the circular sealing tab 420 and defining a first sealing joint 442, compressing the top wall surface 406 of the circular sealing wall 400 against the circular channel base 448 and defining a second sealing joint 450, compressing the exterior wall surface 404 of the circular sealing wall 400 against the interior leg surface 432 of the circular locking leg 430 and defining a third sealing joint 452. The first sealing joint 442, the second sealing joint 450 and the third sealing joint 452 define sealed closure 454 for maintaining the stool 36 within the ostomy chamber 60.

A circular convex shoulder 460 extends from the interior leg surface 432 of the circular locking leg 430. The circular convex shoulder 460 has an aligning orientation 462 with the circular locking foot 438 such that during the sealed closure 454, the exterior wall surface 404 of the circular sealing wall 400 impresses against the circular convex shoulder 460 for maintaining engagement between the circular locking foot 438 and the circular locking channel 440.

Figure 70:
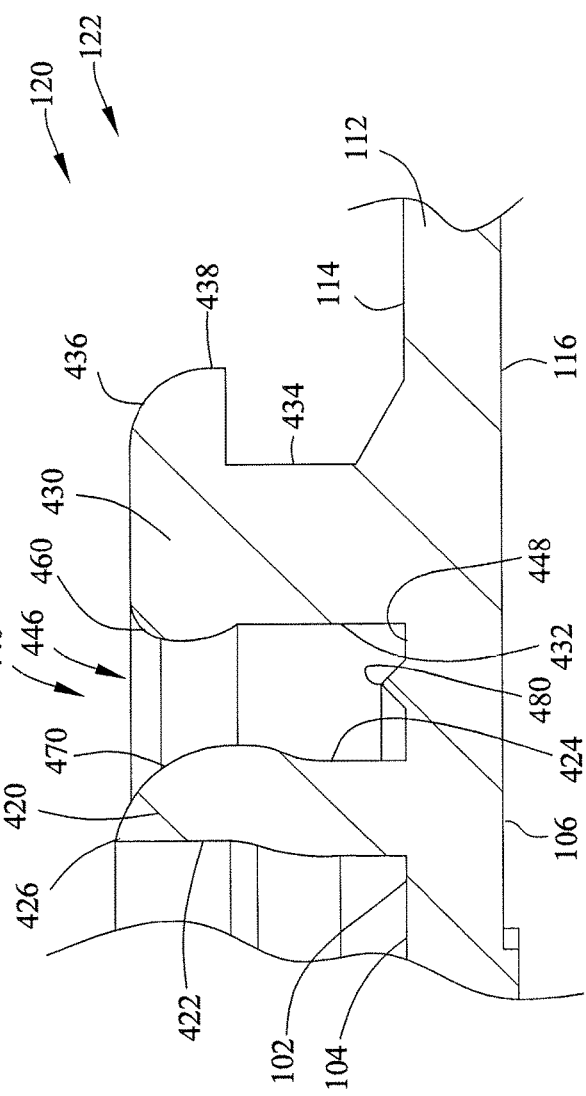
FIG. 70 is an enlarged portion of FIG. 69.
Figure 74:
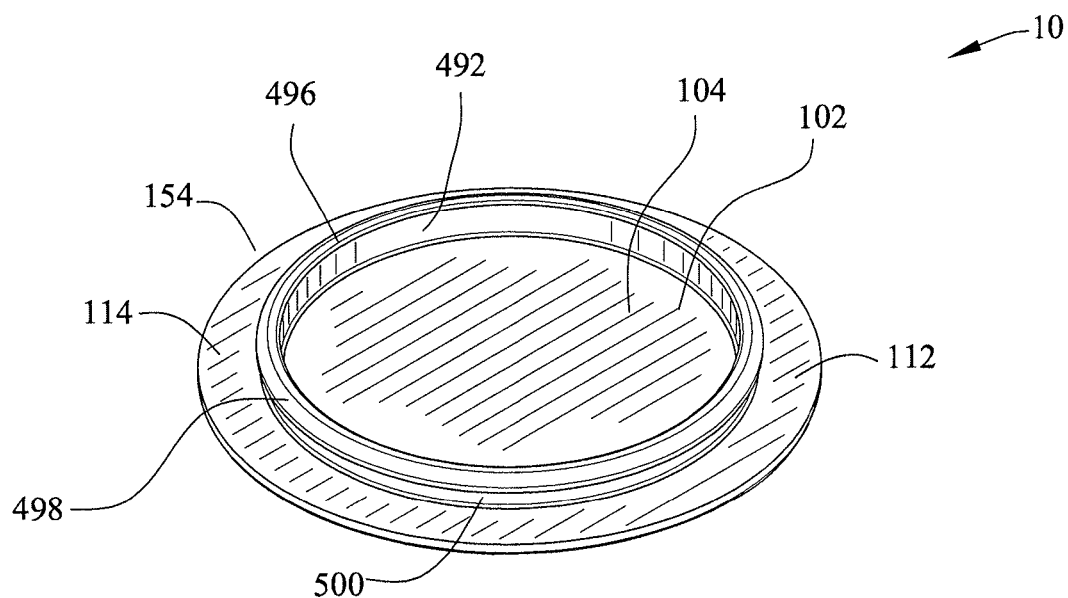
FIG. 74 is an isometric interior view of an additional embodiment for the ostomy closure.
Figure 75:
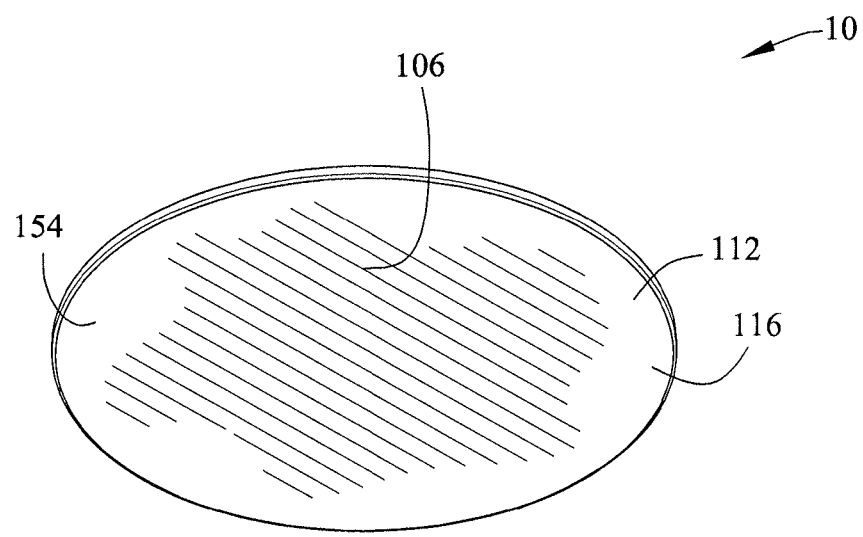
FIG. 75 is an isometric exterior view of FIG. 74.
Figure 76:
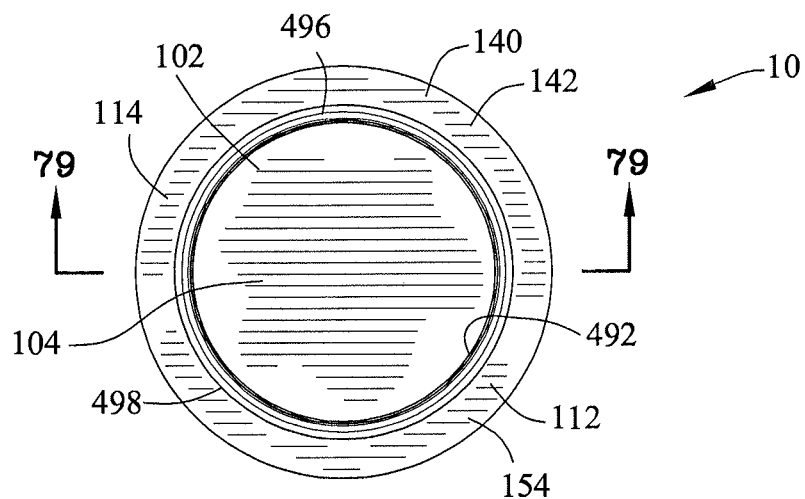
FIG. 76 is a top view of FIG. 74.
Figure 77:
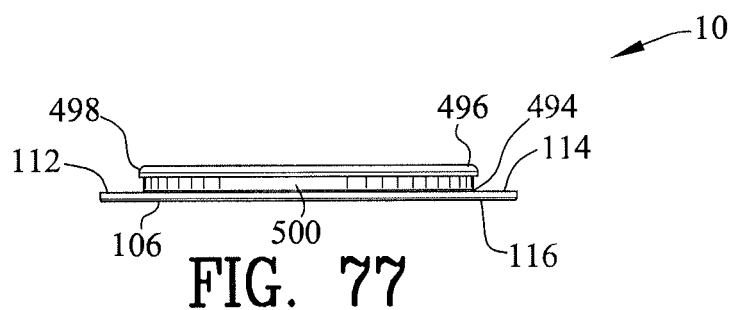
FIG. 77 is a side view of FIG. 76
Figure 78:
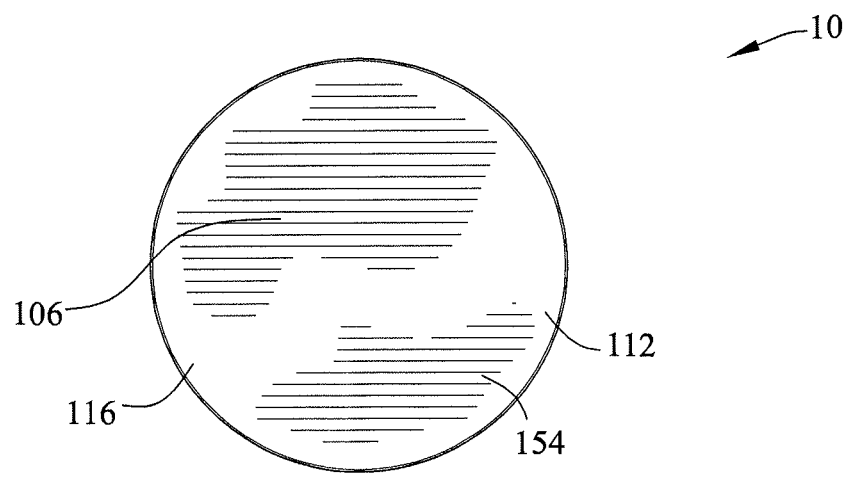
FIG. 78 is a bottom view of FIG. 76.
Figure 84:
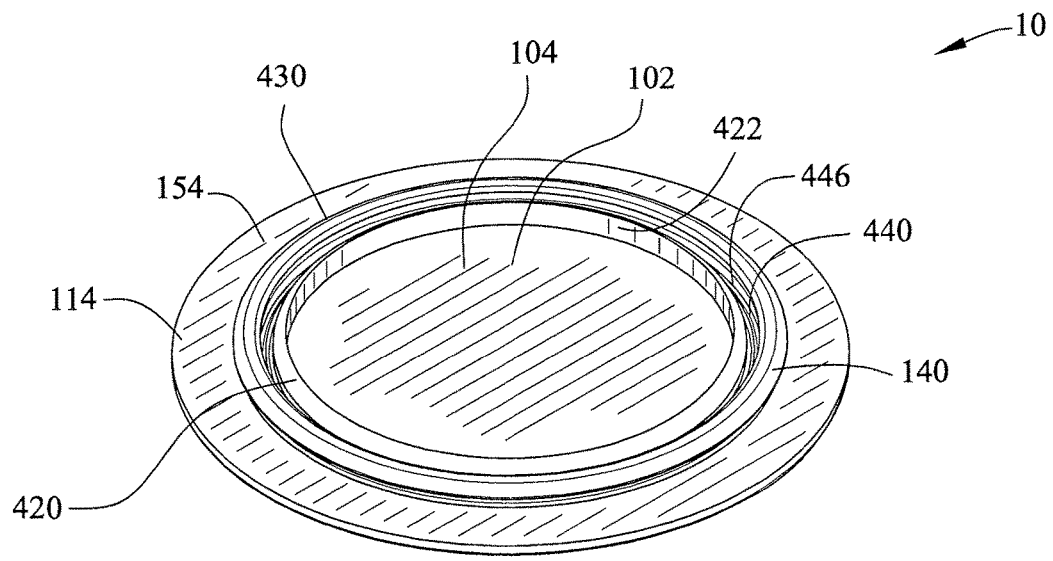
FIG. 84 is an isometric interior view of an additional embodiment for the ostomy closure.
Figure 85:
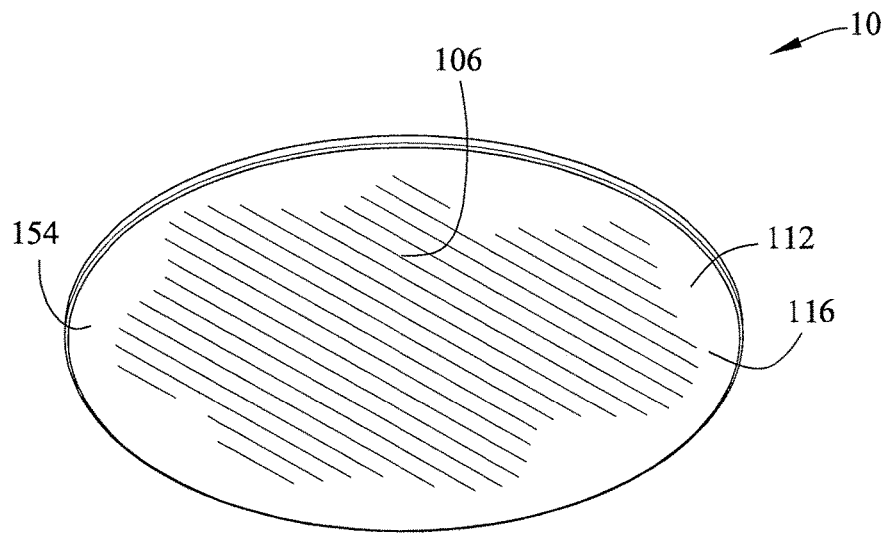
FIG. 85 is an isometric exterior view of FIG. 84.
Figure 86:
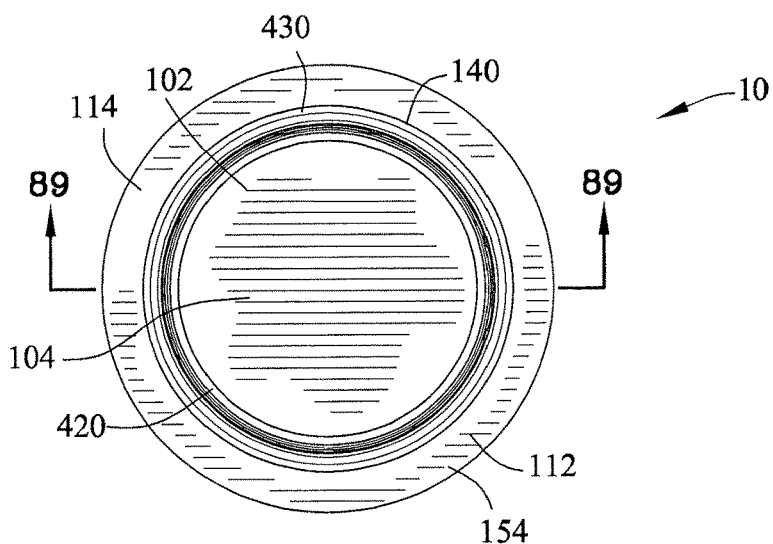
FIG. 86 is a top view of FIG. 84.
Figure 87:
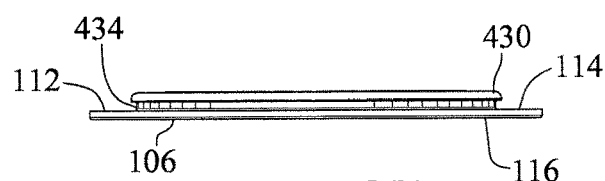
FIG. 87 is a side view of FIG. 86.
Figure 88:
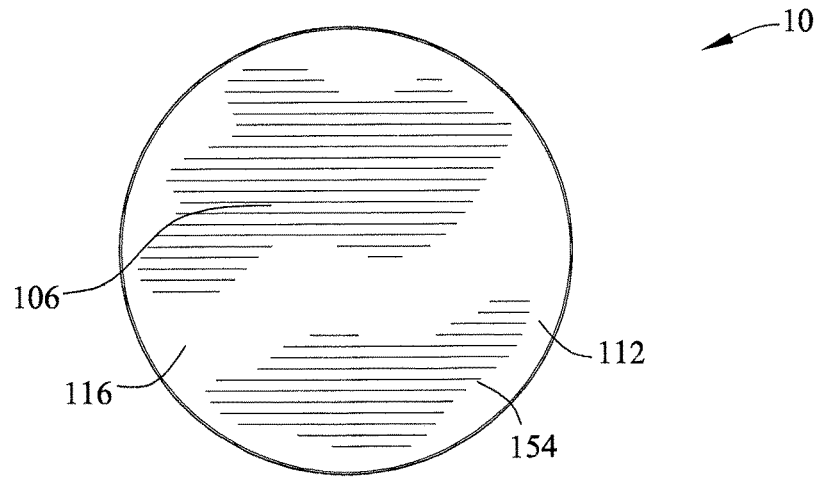
FIG. 88 is a bottom view of FIG. 86.

A circular convex dome 470 as best shown in FIG. 70 extends from the exterior border surface 424 of the circular sealing tab 420. The circular convex dome 470 has a generally aligned orientation 472 with the circular convex shoulder 460 for further compressing the circular sealing wall 400 between the circular sealing tab 420 and the circular locking leg 430.

A circular fin 480 extends from the circular channel base 448 for impressing into the top wall surface 406 of the circular sealing wall 400 for improving the second sealing joint 450.

The top border surface 426 of the circular sealing tab 420 includes an arch surface 482 facing the circular cap channel 446 for facilitating the insertion of the circular sealing wall 400 into the circular cap channel 446.

FIGS. 74-83A illustrate the closure 10 and pouch 12 comprising an ostomy patch 12 having a first flexible layer 40 coupling, to a second flexible layer 50 for defining an ostomy chamber 60. A pouch ring 490 secured to the first flexible layer 40. A cap body 102 defines an interior surface 104 and an exterior surface 106 extending to a peripheral edge 108.

A cylindrical wall 492 extending from the interior surface 104 of the cap body 102 between a proximal end 494 and a distal end 496. A circular laterally extending tab 498 extends from the distal end 496 of the cylindrical wall 492 for defining a mounting channel 500 between the cap body 102 and the circular laterally extending tab 498. The pouch ring 490 is positioned within the mounting channel 500 for defining a coupled position 502. A clamping; device 504 encircling the pouch ring 490 and reducing the pouch ring 490 diameter for impressing the pouch ring 490 against the mounting channel 500 for defining a sealed joint 506.

Figure 94:
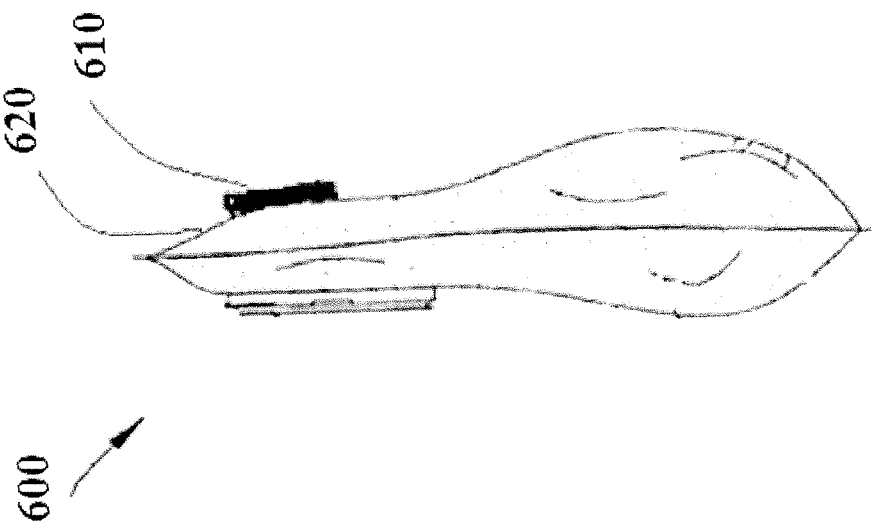
FIG. 94 illustrates a side elevational view of a flexible storage bag attached to an ostomy pouch according to aspects of the disclosure.

FIG. 94 illustrates an embodiment of an ostomy pouch 600 configured for maintaining contents (e.g., stool 36 and/or stool odor 38) within ostomy pouch 600 following use by a patient. Embodiments of ostomy pouch 600 may include a flexible storage bag 610 in a compacted state and adhered to the surface of ostomy pouch 600. Flexible storage bag 610 may be constructed of one unitary piece of material or two or more pieces of material. In some embodiments flexible storage bag 610 may include a first flexible layer and a second flexible layer, wherein the two layers are adhered to each other along a perimeter. Embodiments of flexible storage bag 610 may include a bag base 612 (see FIG. 95) and a bag opening 613 (see FIG. 95). Flexible storage bag 610 may, in some embodiments, define a bag chamber (not shown) accessible via bag opening 613. Flexible storage bag 610 may be constructed of any suitable material that is resistant to permeation by liquids, gases and/or odors so to prevent at least substantially all leakage of the contents from ostomy pouch 600 and at least substantially all leakage of any odors from ostomy pouch 600 associated with the contents, including without limitation, polymeric materials.

Figure 95:
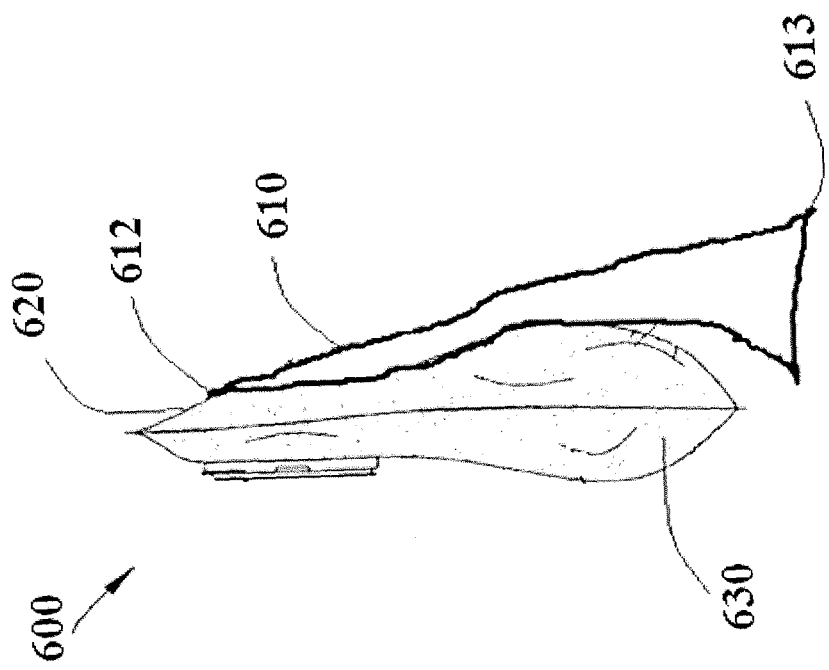
FIG. 95 illustrates a side elevational view of a flexible storage bag attached to an ostomy pouch and in an at least partially deployed configuration according to aspects of the disclosure.

Embodiments of the disclosure may include flexible storage bag 610 being coupled to an exterior surface 620 of ostomy pouch 600, for example in some embodiments by way of bag base 612 (see FIG. 95). Flexible storage bag 610 may be coupled to exterior surface 620 of ostomy pouch 600 by any suitable coupling means, including without limitation glue, hook and loop fasteners, staples, snaps, tapes, double-side tapes, other adhesives and/or any other coupling means. Embodiments of the disclosure may include positioning flexible storage bag 610 at any location on ostomy pouch 600, including a front exterior surface 630 or any side, top or bottom portion of embodiments of ostomy pouch 600, depending on particular configuration of the pouch.

As shown in FIG. 94, flexible storage bag 610 may be provided and attached to ostomy pouch 600 in a compacted configuration by, for example, folding, vacuum forming or other means. In some embodiments, flexible storage bag 610 may be compacted prior to attachment to ostomy pouch 600 or, in other embodiments, following such attachment. In its compacted form, flexible storage bag 610 may be attached to ostomy pouch 600 along any other suitable and exposed surface of flexible storage bag 610 in its compacted form. Advantageously, in this compacted form flexible storage bag 610 is discrete and unnoticed by the patient and others while ostomy pouch 600 is in use and attached the patient.

FIG. 95 illustrates an embodiment of flexible storage bag 610 that is deployed, unfolded or expanded from its compacted form, wherein according to some embodiments, flexible storage bag may be expanded, deployed or unfolded and define a bag enclosure within bag 610 and accessible through bag opening 613 before, during or immediately following the ostomy pouch 600 being filled by a patient with contents (e.g., stool).

Figure 96:
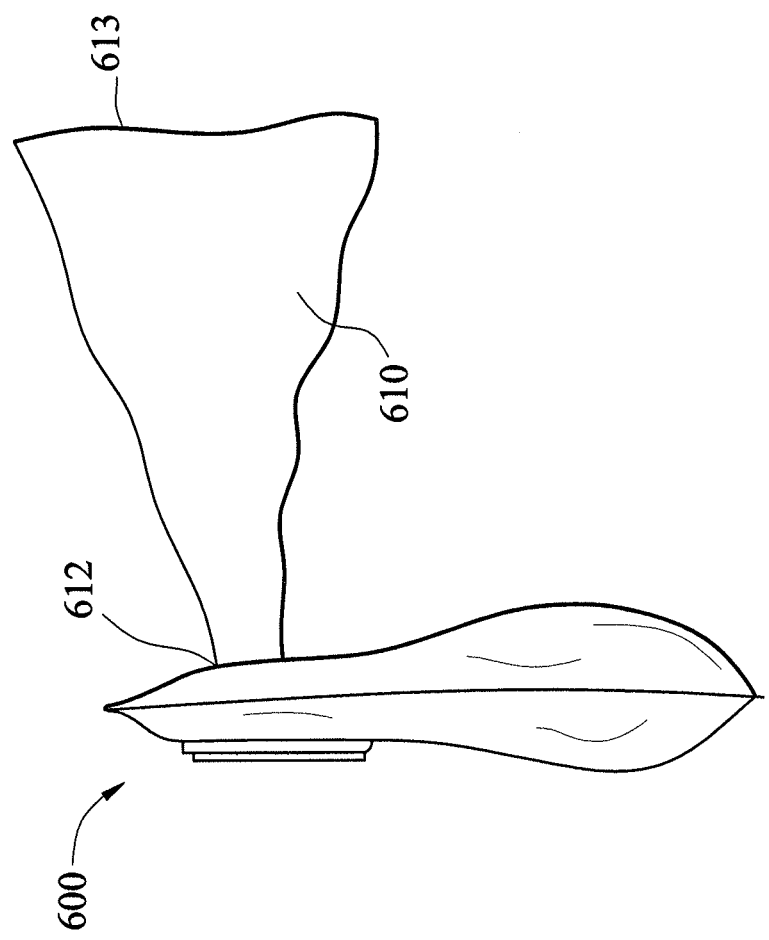
FIG. 96 illustrates a side elevational view of a flexible storage bag attached to an ostomy pouch and in a fully deployed configuration according to aspects of the disclosure.
Figure 97:
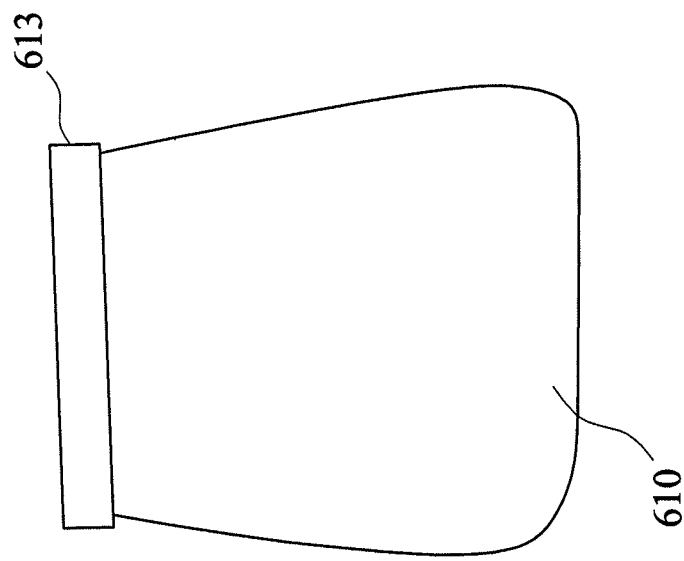
FIG. 97 illustrates a side elevational view of a flexible storage bag attached to an ostomy pouch and at least partially retracted over the ostomy pouch according to aspects of the disclosure.

Following expansion, deployment and/or unfolding from its compacted form, flexible storage bag 610 may be maneuvered outwardly as shown in FIG. 96 and retracted over ostomy pouch 600 for inserting or otherwise moving ostomy pouch 600 into flexible storage bag 610 as shown in FIG. 97.

Figure 98:
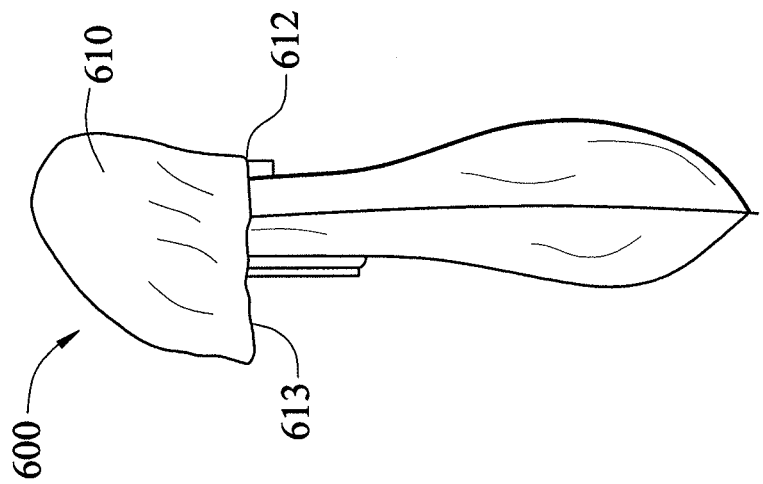
FIG. 98 illustrates a front view of a flexible storage bag encapsulating an ostomy pouch and in securely sealed configuration to maintain ostomy pouch contents therein according to aspects of the disclosure.

As shown in FIG. 98, flexible storage bag 610 may be closed at bag opening 613 after ostomy pouch 600 (not shown) has been fully inserted and encapsulated within flexible storage bag 610. Bag opening 613 may be closed in any suitable way that will be provide a seal that is substantially impenetrable by any liquids, odors and/or other contents contained within ostomy pouch 600. Any suitable means for sealing flexible storage bag 610 securely so as to keep in any and all contents and/or associated odors from ostomy pouch 600 (not shown). For example, bag opening 613 may be closed by an adhesive, drawstring, zip lock or other fastening means. In some embodiments, the adhesive may be contained on flexible storage bag 610 prior to use by a patient. In some embodiments, the adhesive may be applied to flexible storage bag 610 at the time of closure. In some embodiments, the means for securely sealing bag opening 613 may be positioned at or near bag opening 613 or elsewhere on flexible storage bag 610. As a result of the secure seal, flexible storage bag 610 maintains the content (e.g., stool) and the content stool within its confines following closure.

Figure 99:
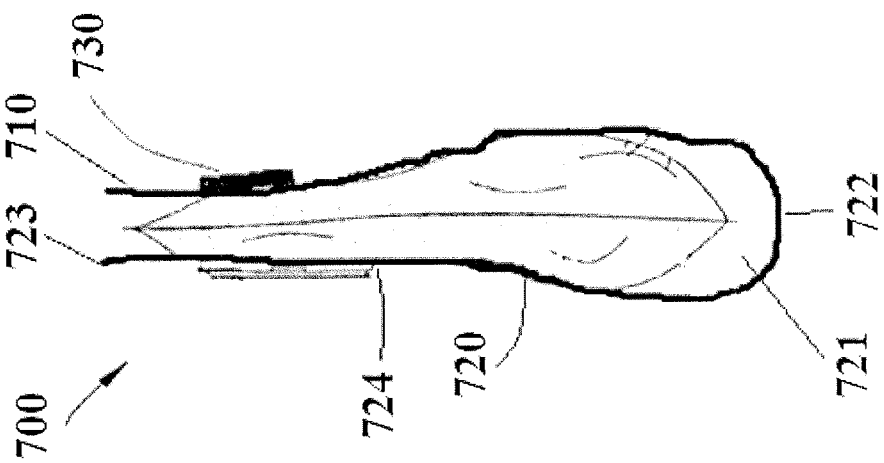
FIG. 99 illustrates a side elevational view of a flexible storage bag engaged with and maintaining within it an ostomy pouch, the flexible storage bag having a first maintaining portion and second portion deployable and retractable over the first portion and ostomy pouch for ostomy pouch disposal purposes according to aspects of the disclosure.

FIG. 99 illustrates an embodiment of an ostomy pouch 700 and flexible storage bag 710 for maintaining content (e.g., stool and/or stool odor) within the confines of ostomy pouch 700 and/or flexible storage bag 710. Ostomy pouch 700 in some embodiments may include flexible storage bag 710 having a first portion 720 and a second portion 730. First portion 720 may include a first bag chamber 721. In FIG. 99 first portion 720 is depicted as a cross-sectional view to illustrate ostomy pouch 700 being contained therein. Embodiments of first portion 720 may be constructed of one unitary piece of material or two or more pieces of material. In some embodiments, first portion 720 may include a first flexible layer and a second flexible layer, wherein the two layers are adhered to each other along a perimeter. First portion 720 may in some embodiments have a first bag base portion 722 and a first bag opening 723. Ostomy pouch 700 may be positioned (e.g., slid) into and within first bag chamber 721 of first portion 720 and maintained therein during use by a patient and/or thereafter, e.g., during and following disposal of ostomy pouch 700.

Figure 100:
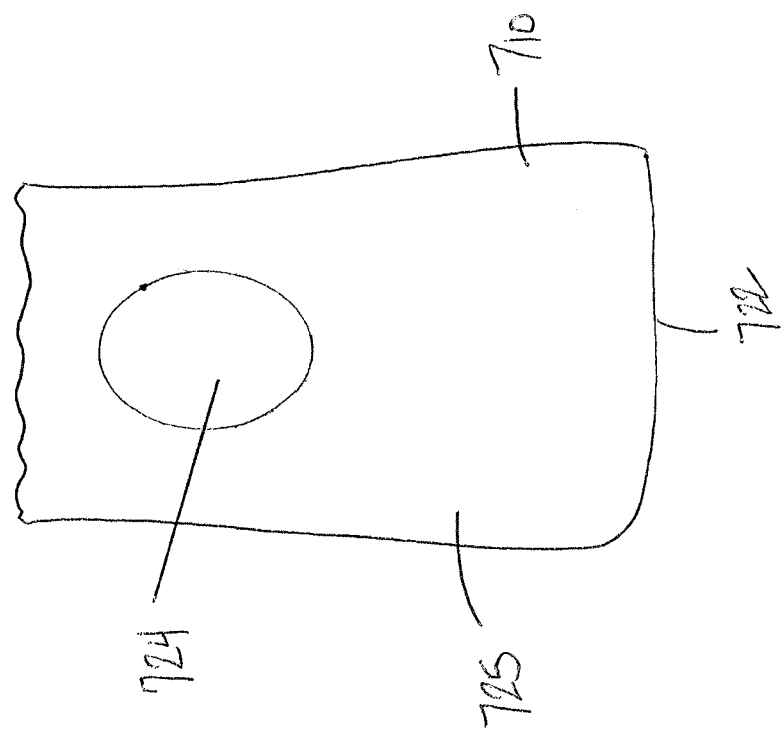
FIG. 100 illustrates a front view of a flexible storage bag according to aspects of the disclosure.

In some embodiments, first portion 720 of flexible storage bag 710 may be attached to ostomy pouch 700, or put differently ostomy pouch 700 may be maintained within flexible storage bag 710, by way of an aperture or hole 724 in a layer 725 of first portion 720, as shown in FIG. 100. More specifically, in some embodiments, hole 724 may be sized and shaped to fit snugly around a flange and/or opening on ostomy pouch 700 so as to maintain ostomy pouch 700 within first portion 720 of flexible storage bag 710. First portion 720 may slide over and encapsulate ostomy pouch 700 similar to glove sliding onto and over a hand. Hole 724 of first portion 720 accounts for and aligns with flange and/or opening of ostomy pouch 700 that receives the stoma and removably attaches to an ostomy pouch mounting plate.

In some embodiments, flexible storage bag 710 may be inserted over and/or removed from ostomy pouch 700 based on a patient's needs. In some embodiments, first portion 720 may include a cap (not shown) wherein the cap has a size and shape of a pouch flange of ostomy pouch 700. The cap may be opened when flexible storage bag 710 is ready for use. In some embodiments, flexible storage bag 710 may be attached to ostomy pouch 700 by, for example, glue, staples, tapes, double-sided tapes, an adhesive layer or any other coupling means. Flexible storage bag 710 may be constructed of any suitable material, including a polymeric material.

Flexible storage bag 710 may also include a second portion 730 coupled to first portion 720 of flexible storage bag 710. While first portion 720 serves to hold ostomy pouch 700, second portion 730 may serve to be unfolded, deployed and/or expanded and otherwise be retracted over ostomy pouch 700 and first portion 720 in a manner similar to how flexible storage bag 610 retracts over and encapsulates ostomy pouch 600. In some embodiments, first portion 720 and second portion 730 are formed as part of the same flexible storage bag 710, as shown in FIG. 99, wherein second portion 730 is integrally attached in a compacted form to a surface of first portion 720. In some embodiments, first portion 720 and second portion 730 may be two separate bags. In some embodiments, second portion 730 of flexible storage bag 710 may be coupled to first portion 720 of flexible storage bag 710 by glue, staples, tapes, double-side tapes, an adhesive layer or any other coupling means. In some embodiments, second portion 730 of flexible storage bag 710 maybe attached to the front or the back of first portion 720 of flexible storage bag 710. Second portion 730 of flexible storage bag 710 may be attached to at least one of the top, bottom, left side, right side or the center of first portion 720. Second portion 730 may be coupled to first portion 720 vertically or horizontally.

As shown in FIG. 99 second portion 730 of flexible storage bag 710 may be compacted by folding, vacuum forming or other means adjacent to first portion 720 of flexible storage bag 710. Second portion 730 of flexible storage bag 710 may be subsequently expanded from first portion 720 of flexible storage bag 710 for defining a second bag enclosure defined by an opening similar to bag opening 613 with respect to flexible storage bag 610. Upon further retraction of the flexible storage bag 710, the bag opening may be retracted over ostomy pouch 700 for defining a second bag pouch enclosure and completely encapsulating ostomy pouch 700 and first portion 720 of flexible storage bag 710 within second portion 730. A bag closure area (not shown) may provide for a sealing closure of second portion 730 so as to encapsulate first portion 720 of flexible storage bag 710 and ostomy pouch 700 within second portion 730 and prevent liquid and gas leakage emanating from content within ostomy pouch 700 and/or first portion 720. Second portion 730 may be securely closed using any suitable means for providing a secure leak-free seal that is substantially impenetrable to liquid and odors or gases associated with content (e.g., stool) provided within ostomy pouch 700, including without limitation adhesives, drawstring closures, knot, zip lock or any other suitable fastening means. As of the system and method embodiments of the subject matter of this disclosure flexible storage bag 710 may maintain content (e.g., stool) and associated odor(s) within second portion 730 following use and/or disposal of ostomy pouch 700.

The present disclosure includes that contained in the appended claims as well as that of the foregoing description. Although this subject matter of the disclosure has been described in its preferred form with a certain degree of particularity, it is understood that the present disclosure of the preferred form has been made only by way of example and that numerous changes in the details of construction and the combination and arrangement of parts may be resorted to without departing from the spirit and scope of the subject matter of the disclosure.

What is claimed is:

1. An ostomy pouch comprising:
an ostomy chamber formed by a first flexible layer with a pouch aperture and a second flexible layer, the second flexible layer coupled to the first flexible layer;
a pouch flange fixed to the first flexible layer at the pouch aperture and for conveying stool from the individual to the ostomy chamber; and
an ostomy closure for sealing the ostomy pouch after removal from an ostomy mounting plate,
wherein:
the ostomy pouch disengages from the ostomy mounting plate for disposal of the stool, and
the ostomy closure comprises a flexible storage bag having a bag chamber extending between a bag base and a bag opening, and having a bag closure, wherein the bag base is directly in contact with and adhered to the exterior surface of the second flexible layer of the ostomy pouch, the bag opening is expandable and retractable over the ostomy pouch and positions the ostomy pouch within the bag chamber; and the bag closure seals the bag chamber and encapsulates the ostomy pouch within the bag chamber to maintain the stool and stool odor within the flexible storage bag during and following disposal of the ostomy pouch.

2. The ostomy pouch as set forth in claim 1, wherein the bag base is directly in contact with and adhered to the exterior surface of the second flexible layer of the ostomy pouch by at least one of glue, staples, tapes, double-sided tapes or an adhesive layer.

3. The ostomy pouch as set forth in claim 1, wherein the bag base is directly in contact with and adhered to the exterior surface of the second flexible layer of the ostomy pouch vertically or horizontally.

4. The ostomy pouch as set forth in claim 1, wherein the bag chamber is compacted by at least one of folding or vacuum forming adjacent to the exterior surface of the second flexible layer of the ostomy pouch.

5. The ostomy pouch as set forth in claim 4, wherein the bag chamber is expanded from the exterior surface of the second flexible layer of the ostomy pouch.

6. The ostomy pouch as set forth in claim 1, wherein the bag closure includes at least one of a drawstring closure, knot, zip lock, adhesive or other fastener.

7. An ostomy pouch comprising:
an ostomy chamber formed by a first flexible layer with a pouch aperture and a second flexible layer, the second flexible layer coupled to the first flexible layer;
a pouch flange fixed to the first flexible layer at the pouch aperture and for conveying stool from the individual to the ostomy chamber; and
an ostomy closure for sealing the ostomy pouch after removal from an ostomy mounting plate,
wherein:
the ostomy pouch disengages from the ostomy mounting plate for disposal of the stool, and
the ostomy closure comprises a flexible storage bag having a first portion and a second portion,
the first portion formed by a first flexible layer having an aperture and a second flexible layer, the second flexible layer of the first portion coupled to the first flexible layer of the first portion, the first bag chamber extending between a first bag base and a first bag opening, wherein the first portion encapsulates the ostomy pouch within the first bag chamber and the aperture is sized and fits around the pouch flange to maintain the ostomy pouch within the first bag chamber, and
the second portion having a second bag closure and a second bag chamber extending between a second bag base and a second bag opening, wherein the second bag base is directly in contact with and adhered to the exterior surface of the second flexible layer of the first portion of the flexible storage bag and the second bag opening is expandable and retractable over the first portion of the flexible storage bag and the ostomy pouch and positions the first portion of the flexible storage bag and the ostomy pouch within the second bag chamber, and the second bag closure seals the second bag chamber and encapsulates the first portion of the flexible storage bag and the ostomy pouch within the second bag chamber to maintain the stool and stool odor within the flexible storage bag during and following disposal of the ostomy pouch.

8. The ostomy pouch as set forth in claim 7, wherein the first portion and the second portion are from the same flexible storage bag.

9. The ostomy pouch as set forth in claim 7, wherein the first portion and the second portion are from at least two bags.

10. The ostomy pouch as set forth in claim 7, wherein the second bag base is directly in contact with and adhered to the first portion by at least one of glue, staples, tapes, double-sided tapes, or an adhesive layer.

11. The ostomy pouch as set forth in claim 7, wherein the second bag base is directly in contact with and adhered to the first portion on at least one of the top, bottom, left side, right side or the center of the first portion.

12. The ostomy pouch as set forth in claim 7, wherein the second bag base is directly in contact with and adhered to the first portion vertically or horizontally.

13. The ostomy pouch as set forth in claim 7, wherein the second portion is compacted by at least one of folding or vacuum forming adjacent to the first portion.

14. The ostomy pouch as set forth in claim 13, wherein the second portion is expanded from the first portion.

15. The ostomy pouch as set forth in claim 7, wherein the bag closure includes at least one of a drawstring closure, knot, zip lock, adhesive or other fastener.

* * * * *